(12) United States Patent
van Wyk et al.

(10) Patent No.: US 9,682,114 B2
(45) Date of Patent: Jun. 20, 2017

(54) **PLANT EXTRACTS OF *PTAEROXYLON OBLIQUUM* NAND COMPOUNDS HAVING ANTIMICROBIAL AND ANTIHELMINTHIC ACTIVITY**

(71) Applicant: UNIVERSITY OF PRETORIA, Pretoria (ZA)

(72) Inventors: Candice van Wyk, Pretoria (ZA); Francien Botha, Pretoria (ZA); Jacobus Nicolaas Eloff, Pretoria (ZA); Thanyani Emelton Ramadwa, Tshilwavhusiku (ZA)

(73) Assignee: University of Pretoria, Pretoria (ZA)

( * ) Notice: Subject to any disclaimer, the term of this patent is extended or adjusted under 35 U.S.C. 154(b) by 0 days.

(21) Appl. No.: 14/778,454

(22) PCT Filed: Mar. 20, 2014

(86) PCT No.: PCT/IB2014/059993
§ 371 (c)(1),
(2) Date: Sep. 18, 2015

(87) PCT Pub. No.: WO2014/147581
PCT Pub. Date: Sep. 25, 2014

(65) Prior Publication Data
US 2016/0279185 A1 Sep. 29, 2016

(30) Foreign Application Priority Data
Mar. 20, 2013 (ZA) .................................. 2013/02111

(51) Int. Cl.
| A61K 36/75 | (2006.01) |
| A61K 31/352 | (2006.01) |
| A01N 43/90 | (2006.01) |
| C07D 493/04 | (2006.01) |

(52) U.S. Cl.
CPC .............. *A61K 36/75* (2013.01); *A01N 43/90* (2013.01); *A61K 31/352* (2013.01); *C07D 493/04* (2013.01)

(58) Field of Classification Search
None
See application file for complete search history.

(56) References Cited

PUBLICATIONS

Soyelu et al. In African Journal of Biotechnology 11(14), 2476-3481 (2012).*

Nielsen et al. in BMC Complementary and Alternative Medicine 12:74, 1-6 (2012).*
Dean et al. in J. Chem. Soc. C, 114-116 (1966).*
Soyelu, O.T. and Masika, P.J. (2012) Antibacterial and antioxidant activities of some selected plants used for the treatment of cattle wounds in the Eastern Cape. African Journal of Biotechnology. vol. 11 (14): 3476-3481.
Nielsen, Trine R.N. et al. (2012) Antimicrobial activity of selected South African medicinal plants. BMC Complementary and Alternative Medicine. vol. 12 (74): 6 pages.
South African Association of Botanists (SAAB)—Annual Meeting 2012. Abstracts of papers and posters presented at the 38th Annual Congress of the South African Association of Botanists held at the University of Pretoria, Pretoria, South Africa, Jan. 15-18, 2012. South African Journal of Botany. vol. 79: 173-240.
Cock, I.E., and van Vuuren, S.F. (2014) Anti-Proteus activity of some South African medicinal plants: their potential for the prevention of rheumatoid arthritis. Inflammopharmacology. 22: 23-36.
International Search Report from the International Searching Authority for Application No. PCT/IB2014/059993, dated May 22, 2014.

* cited by examiner

*Primary Examiner* — Dennis Heyer
(74) *Attorney, Agent, or Firm* — Meunier Carlin & Curfman LLC

(57) ABSTRACT

This invention relates to an antimicrobial and antihelminthic agent comprising a compound of formula (I), to a process for extracting the antimicrobial and/or antihelminthic agent from plant material, to a composition containing the antimicrobial and/or antihelminthic agent, and to a plant extract containing the antimicrobial and/or antihelminthic agent.

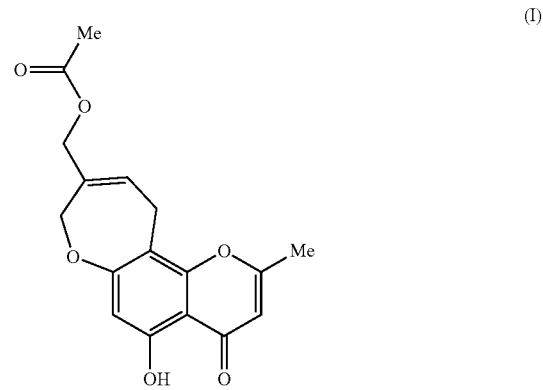

9 Claims, 16 Drawing Sheets

|      |   | CEF               |      | EMW |                       |     | BEA |                           |
|------|---|-------------------|------|-----|-----------------------|-----|-----|---------------------------|
| SBA  | : | S. birrea acetone | POA  | :   | P. obliquum acetone   |     |     |                           |
| HCA  | : | H. caffrum acetone| RMA  | :   | R. melanophloeos acetone |  |     |                           |

PLANT EXTRACTS OF *PTAEROXYLON OBLIQUUM* NAND COMPOUNDS HAVING ANTIMICROBIAL AND ANTIHELMINTHIC ACTIVITY

BACKGROUND OF THE INVENTION

This invention relates to an antimicrobial and antihelminthic agent, to a process for extracting the antimicrobial/antihelminthic agent from plant material, to a composition containing the antimicrobial/antihelminthic agent, and to a plant extract containing the antimicrobial/antihelminthic agent.

In most countries of subtropical Africa, bacterial and fungal infections represent an increasing problem, particularly with patients suffering from severe immune deficiencies, such as AIDS (Atindehou et al., 2002). There are also serious problems in controlling helminth parasites. Both with microorganisms and parasites there is a serious problem of resitance developing against therapeutic products. Moreover, the validation of medicinal plant based therapies is imperative for African developing countries, as more than 70 percent of the population use such remedies (Pousset, 1994).

Although various studies in the vast and still growing literature on traditional medicine have reported the indigenous use of medicinal plants in the treatment of oral diseases, oral health-related problems have not been particularly singled out for comment (Tapsoba and Deschamps, 2006).

It is clear that reliance on plant products for the management of oral and other health-related problems is common around the world (Tapsoba and Deschamps, 2006). Publications are found on this topic not only in African countries such as Equatorial Guinea (Akendengue, 1992), Madagascar (Novy, 1997), and South Africa (Lin et al., 1999) but also in other parts of the world including Nepal (Manandhar, 1998), Guatemala (Hunter and Arbona, 1995), and Palestine (Ali-Shtayeh et al., 2000).

Medicinal plants have attracted considerable research attention as new sources of antimicrobial agents against, for instance, *Candida* infections (Taweechaisupapong et al., 2005). A wide variety of plant extracts have antimicrobial effects and anti-inflammatory properties (Kweifio-Okai, 1991; Matsuda et al., 1997; Taweechaisupapong et al., 2000a; Taweechaisupapong et al., 2000b; Atindehou et al., 2002; Mahasneh, 2002; Taweechaisupapong et al., 2002a; Taweechaisupapong et al., 2002b, Shai et al., 2008). Several herbal extracts have been added to some cosmetics and health-care preparations (Taweechaisupapong et al., 2005).

SUMMARY OF THE INVENTION

According to the invention, there is provided a process for preparing an extract of a plant of the genus *Ptaeroxylon* or, the extract comprising an antimicrobial/antihelminthic agent, the process including the steps of treating collected plant material with a solvent to extract a fraction having antifungal activity, antimicrobial activity and antihelminthic activity, separating the extraction solution from the rest of the plant material, removing the solvent from the extraction solution and recovering the extract. The extract so recovered may be further purified, e.g. by way of suitable solvent extraction procedures.

This invention also relates to the use of a plant extract made of plants of the group comprising the genus *Ptaeroxylon* and having antifungal, antibacterial and antihelminthic activity.

The extract may be prepared from plant material such as the stems, leaves and roots of said plants of the genus *Ptaeroxylon*.

The genus *Ptaeroxylon* include trees abundant in southern Africa.

In one application of the invention, the active antimicrobial/antihelminthic extract is obtained from the species *Ptaeroxylon obliquum*. Bioassays conducted by the Applicant have indicated that certain of the extracts possess antifungal, antimicrobial and antihelminthic activity.

The Applicant has found that at least one purified fraction has good antifungal, antimicrobial and antihelminthic activity, and the active principle in the fraction was identified by conventional chemical techniques including nuclear magnetic resonance, and was found to be a compound of the structural formula:

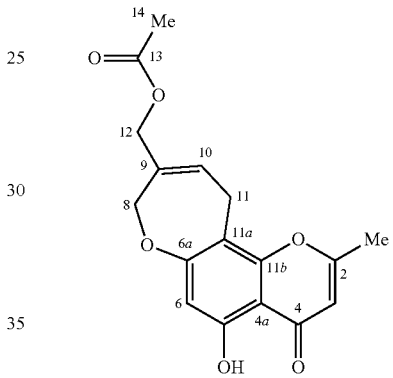

In accordance with S.I. nomenclature, the active principle (1) is the compound 8,11-Dihydro-5-hydroxy-12-hydroxymethyl-2-methyl-4Hpyrano[2,3-g] [1]benzoxepin-4-one 12-O-acetate. Based on the species from which this compound was isolated it is given the trivial name of obliquumol.

According to another aspect of the invention, there is provided a process for preparing an extract of a plant of the genus *Ptaeroxylon*, the extract comprising an antimicrobial/antihelminthic agent.

Distilled water, acetone or hexane may be used as extractants. Powdered plant material may be extracted with solvent, lightly shaken, sonicated and allowed to stand for a predetermined time at room temperature. The extracts may then be centrifuged, e.g. 4000×g for 15 minutes. The supernatant may be retained and filtered, for example, through Whatman #1 filter paper. Extracts may be stored at below zero degrees temperatures, for example, −18° C., to limit chemical decomposition.

The extract may be dried to remove moisture, e.g. by spray-drying, freeze-drying or vacuum drying, to form a free-flowing powder.

The invention extends to a composition having antimicrobial and/or antihelminthic activity comprising an extract as described above. The composition may be a pharmaceutical composition.

The composition may be admixed with a pharmaceutical excipient, diluent or carrier and optionally it is prepared in unit dosage form.

The invention also extends to the use of an extract as described above in the manufacture of a medicament having antimicrobial and/or antihelminthic activity and to an extract as described above for use as a medicament having antifungal activity.

The invention further extends to the use of the compound or the composition described above in treating or preventing an infection in a subject. It will be appreciated that the infection may be selected from the group consisting of fungal, bacterial or helminthic infections. It will further be appreciated that the subject may be a mammal, preferably a human. Alternatively, the subject may be a plant.

The compound set out above is a novel compound and the invention extends to the compound and certain analogues or derivatives of this compound having antimicrobial and/or antihelminthic properties. The molecules chosen as the analogues or derivatives are intended to affect the properties of the compound with the aim of increasing the activity of the active ingredient.

The invention extends also to a composition or formulation having antimicrobial and/or antihelminthic activity, in which the active ingredient is an extract as described above.

The antimicrobial and/or antihelminthic agent may be an isolated natural chemical or a synthetic chemical compound of the formula

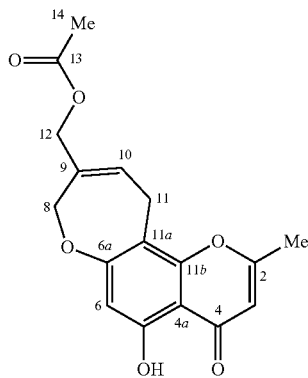 [SMILES: CC(=O)OCC1=CCc2c(cc(O)c3c(=O)cc(C)oc23)OC1]

or derivatives or analogues thereof, as set out before.

The antimicrobial and/or antihelminthic composition or formulation may consist of the antimicrobial and/or antihelminthic agent admixed with a pharmaceutical excipient, diluent or carrier. Other suitable additives, including a stabilizer and such other ingredients as may be desired may be added.

The invention extends to the use of the compound or its derivatives or analogues in the manufacture of a medicament having antimicrobial and/or antihelminthic activity.

The invention further extends to compound or its derivatives or analogues as set out before, for use as a medicament having antimicrobial and/or antihelminthic activity.

The invention further extends to methods of treatment of a subject for an infection, wherein the method comprises administering an effective amount of the compound described above to a subject. It will be appreciated that the infection may be selected from the group consisting of fungal, bacterial or helminthic infections. It will further be appreciated that the subject may be a mammal, preferably a human. Alternatively, the subject may be a plant.

A method has been described herein for extracting a compound having antimicrobial and/or anthelminthic activity from plant material obtained from a plant of the genus *Ptaeroxylon*. The invention thus extends to an extract obtained from plant material of the genus *Ptaeroxylon* and containing a substantially pure compound as set out above.

The invention extends also to a composition containing an effective quantity of the compound as set out above, or its derivatives or analogues as set out before, to have an antimicrobial and/or antihelminthic effect when applied.

The compound or composition of the invention may be used on a subject having a bacterial infection and/or the method of the invention may be performed on a subject having a bacterial infection, wherein the infection is caused by a bacterium selected from the group consisting of *Acinetobacter* spp., *Actinobacillus* spp., *Actinomycetes* spp., *Aeromonas* spp., *Bacillus* spp., *Bordetella* spp., *Borrelia* spp., *Brucella* spp., *Campylobacter* spp., *Chlamydia* spp., *Clostridium* spp., *Corynebacterium* spp., *Enterobacter* spp., *Enterococcus* spp., *Erwinia* spp., *Erysipelothrix* spp., *Escherichia* spp., *Francisella* spp., *Klebsiella* spp., *Haemophilus* spp., *Legionella* spp., *Leptospira* spp., *Listeria* spp., *Moraxella* spp., *Mycobacterium* spp., *Mycoplasma* spp., *Neisseria* spp., *Nocardia* spp., *Pasteurella* spp., *Pseudomonas* spp., *Rickettsia* spp., *Salmonella* spp., *Shigella* spp., *Spirillum* spp., *Staphylococcus* spp., *Streptobacillus* spp., *Streptococcus* spp., *Streptomyces* spp., *Treponema* spp., *Vibrio* spp., *Yersinia* spp. and *Xanthomonas* spp. Preferably, the bacterium is selected from the group consisting of *Escherichia coli*, *Enterococcus faecalis*, *Mycobacterium aurum*, *Mycobacterium bovis*, *Mycobacterium fortuitum*, *Mycobacterium smegmatis*, *Pseudomonas aeruginosa*, *Staphylococcus aureus* and *Salmonella typhi*.

The compound or composition of the invention may be used on a subject having a fungal infection and/or the method of the invention may be performed on a subject having a fungal infection, wherein the infection is caused by a fungus selected from the group consisting of *Altemaria* spp., *Aspergillus* spp., *Candida* spp., *Cercospora* spp., *Cladosporium* spp., *Colletotrichum* spp., *Cryptococcus* spp., *Diplodia* spp., *Fusarium* spp., *Guignardia* spp., *Monilinia* spp., *Penicillium* spp., *Phytophthora* spp., *Plasmopara* spp., *Podosphaera* spp., *Puccinia* spp., *Pythium* spp., *Rhizoctonia* spp., *Rhizopus* spp., *Sclerotinia* spp., *Sphaerotheca* spp., *Trichoderma* spp., *Venturia* spp. and *Verticillium* spp. Preferably, the fungus is selected from the group consisting of *Aspergillus fumigatus*, *Aspergillus niger*, *Aspergillus parasiticus*, *Candida albicans*, *Colletotrichum gloeosporioides*, *Cryptococcus neoformans*, *Fusarium oxysporum*, *Penicillium digitum*, *Penicillium expansum*, *Penicillium italicum*, *Penicillium janthinellum*, *Trichoderma harzianum* and *Rhizoctonia solani*.

The compound or composition of the invention may further be used on a subject having a helminthic infection and/or the method of the invention may be performed on a subject having a helminthic infection, wherein the infection is caused by a helminth selected from the group consisting of *Ascaris* spp., *Ancylostoma* spp., *Haemonchus* spp., *Strongoloides* spp., *Necator* spp., *Trichuris* spp. and *Uncinaria* spp. Preferably, the helminth is *Haemonchus contortus*.

The invention and its efficacy will now be further described, without limitation of the scope of the invention, with reference to the following examples and drawings.

BRIEF DESCRIPTION OF THE FIGURES

Non-limiting embodiments of the invention will now be described by way of example only and with reference to the following figures.

DETAILED DESCRIPTION OF THE INVENTION

Figure 1:
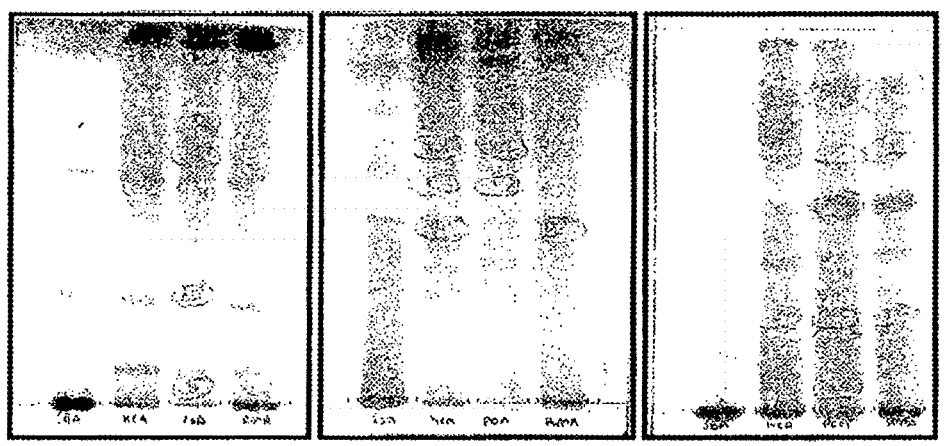
FIG. 1: TLC Reference plates

The present invention will now be described more fully hereinafter with reference to the accompanying drawings, in which some, but not all embodiments of the invention are shown.

The invention as described should not to be limited to the specific embodiments disclosed and modifications and other embodiments are intended to be included within the scope of the invention. Although specific terms are employed herein, they are used in a generic and descriptive sense only and not for purposes of limitation.

As used throughout this specification and in the claims which follow, the singular forms "a", "an" and "the" include the plural form, unless the context clearly indicates otherwise.

The terminology and phraseology used herein is for the purpose of description and should not be regarded as limiting. The use of the terms "comprising", "containing", "having" and "including" and variations thereof used herein, are meant to encompass the items listed thereafter and equivalents thereof as well as additional items.

In its broadest form, the present invention relates to crude extracts, fractions and/or isolated compounds derived from the leaves of a *Ptaeroxylon obliquum* plant. The crude extracts, fractions and/or isolated compounds provide antibacterial, antifungal and antihelminthic activity. The extracts are for use in the prevention and treatment of bacterial, fungal and/or helminthic infections in a subject. Preferably, the crude extracts, fractions and/or isolated compounds are for use in the treatment of immune compromised subjects.

Those skilled in the art will appreciate that there are a number of methods for preparing extracts from crude plant material. These methods include, among others, cutting, chopping, macerating and/or grinding raw or dried plant material and adding at least one solvent in order to obtain a plant extract. It will also be appreciated that the crude plant material may be fresh material or dry plant material.

The solvent may be an organic solvent. Organic solvents typically used in the preparation of plant extracts include but are not limited to ethanol, methanol, butanol, acetone, dichloromethane, chloroform, glycerine, hexane, ethyl acetate, propylene glycol, water and/or mixtures thereof.

As used herein the term "crude extract" refers to a concentrated preparation of a plant extract obtained by removing secondary metabolites from the plant material with the aid of a suitable solvent. This may be done, for example, by submerging the crude plant material in a suitable solvent, removing the solvent and consequently evaporating all or nearly all of the solvent. As used herein the term "purified extract" refers to an extract obtained by separating the constituent parts of a crude extract from each other. By way of a non-limiting example, the constituent parts of the crude extract may be separated from one another by separating the polar constituents from the non-polar constituents. In so doing the active polar and/or non-polar constituents may thus be concentrated.

As described herein the crude extracts, fractions and/or isolated compounds of the invention are suitable for oral, nasal, topical (including buccal and sublingual), rectal, vaginal, aerosol, intravenous, cutaneous or subcutaneous use on a subject. The subject may include a plant, a living animal, preferably a mammal and most preferably a human.

The crude extracts, fractions and/or isolated compounds can be prepared in any desired delivery form known in the art of pharmaceuticals for example, the extract may be prepared as a tablet, capsule, tincture, power, inhalant, syrup, spray, lozenge, granule and/or liquid. Other conventional formulations, including known carriers and additives, will be readily apparent to those skilled in the art.

The crude extracts, fractions and/or isolated compounds may be formulated as a pharmaceutical composition, by methods know to those skilled in the art. Pharmaceutically acceptable ingredients may be used. The term "pharmaceutically acceptable" refers to properties and/or substances which are acceptable for administration to a subject from a pharmacological or toxicological point of view. Further "pharmaceutically acceptable" refers to factors such as formulation, stability, patient acceptance and bioavailability which will be known to a manufacturing pharmaceutical chemist from a physical/chemical point of view.

The "suitable forms" of the pharmaceutical composition may be combined with "pharmaceutically acceptable carriers" and other elements known in the art to produce tablets, capsules, tinctures, powers, inhalants and/or liquids. The pharmaceutical composition may further be combined with other ingredients which promote the absorption of the extract into the body.

The compounds or derivatives of the present invention may be used in the form of pharmaceutically-acceptable salts derived from inorganic or organic acids. The term "pharmaceutically-acceptable salt" includes salts that are, within the scope of sound medical judgment, suitable for use in contact with the tissues of humans and animals without undue toxicity, irritation, and allergic response, and are proportionate with a reasonable benefit to risk ratio. Pharmaceutically-acceptable salts are well known in the art. The salts may be prepared in situ during the final isolation and purification of the compounds of the invention or separately by reacting a free base with a suitable acid.

By "pharmaceutically acceptable carrier" is meant a solid or liquid filler, diluent or encapsulating substance which may be safely used for the administration of the extract, pharmaceutical composition and/or medicament to a subject.

The dosage of any compositions of the present invention will vary depending on the symptoms, age and body weight of the patient, the nature and severity of the disorder to be treated or prevented, the route of administration, and the form of the subject composition. Any of the subject compositions may be administered in a single dose or in divided doses. Dosages for the compositions of the present invention may be readily determined by techniques known to those of skill in the art or as taught herein.

It will be appreciated that the crude extract, fraction, isolated compound and/or pharmaceutical composition comprising the crude extracts, fractions and/or isolated compounds may be used in applications for human, animal and/or veterinary products. Further due to the nature of the compounds of the present invention it will be appreciated that the subject may also be a non-human organism, such as a plant.

The term "preventing", when used in relation to an infectious disease, or other medical disease or condition, is well understood in the art, and includes administration of a composition which reduces the frequency of, or delays the onset of, symptoms of a medical condition in a subject relative to a subject which does not receive the composition. Prevention of an infection includes, for example, reducing the number of diagnoses of the infection in a treated population versus an untreated control population, and/or delaying the onset of symptoms of the infection in a treated population versus an untreated control population.

The term "prophylactic or therapeutic" treatment is well known to those of skill in the art and includes administration to a subject of one or more of the subject compositions. If the composition Is administered prior to clinical manifestation of the unwanted condition (e.g., disease or other unwanted state of the subject) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The term "treating" is recognised by those of skill in the art and refers to curing, as well as ameliorating at least one symptom of a condition or disorder The use of the crude extracts, fractions, isolated compounds and/or pharmaceutical compositions containing the compound of the invention entails administration of an effective amount of the crude extract, fraction, isolated compound and/or pharmaceutical composition containing the compound to a subject in order to prevent or treat a condition. The term "effective amount" or "effective dose" in the context of preventing or treating a condition refers to the administration of an amount of the active plant extract to an individual in need of treatment, either a single dose or several doses of the extract or pharmaceutical composition containing the extract, fraction and/or isolated compound. As will be appreciated by those of ordinary skill in this art, the effective amount of a composition may vary depending on such factors as the desired biological endpoint, the drug to be delivered, the composition of any additional active or inactive ingredients, the target tissue and several other factors.

The precise time of administration and amount of any particular subject composition that will yield the most effective treatment in a given patient will depend upon the activity, pharmacokinetics, and bioavailability of the subject composition, physiological condition of the patient (including age, disease type and stage, general physical condition, responsiveness to a given dosage, sex and type of medication), route of administration, and other factors which are known to those in the art. The guidelines presented herein may be used to optimize the treatment, e.g., determining the optimum time and/or amount of administration, which will require no more than, routine experimentation consisting of monitoring the subject and adjusting the dosage and/or timing.

Toxicity and therapeutic efficacy of compositions of the invention may be determined by standard pharmaceutical procedures in cell cultures or experimental animals, such as by determining the $LD_{50}$ and the $ED_{50}$. Data obtained from the cell cultures and/or animal studies may be used to formulating a dosage range for use in humans. The dosage of any subject composition lies preferably within a range of circulating concentrations that include the $ED_{50}$ which has little or no toxicity. The dosage may vary within this range depending upon the dosage form employed and the route of administration utilized. For compositions of the present invention, the therapeutically effective dose may be estimated initially from cell culture assays.

The compounds obtained from an extract may be further purified and/or modified by means of synthetic organic chemistry methods which are well-known in the art. The compounds of the invention may also be produced by synthetic organic chemistry methods well-known in the art.

The invention also relates in part to a method of treating an infection in a subject comprising administering to a subject in need thereof a therapeutically effective amount of a compound or composition of the present invention.

It will be appreciated that the compounds of the present invention have antimicrobial and antihelminthic activity. As used herein the term "antimicrobial" includes bacteria, fungi, protozoans and viruses.

The infection may be a bacterial infection caused by a bacteria selected from, but not limited to, the following genera *Acinetobacter, Actinobacillus, Actinomycetes, Aeromonas, Bacillus, Bordetella, Borrelia, Brucella, Campylobacter, Chlamydia, Clostridium, Corynebacterium, Enterobacter, Enterococcus, Erwinia, Erysipelothrix, Escherichia, Francisella, Klebsiella, Haemophilus, Legionella, Leptospira, Listeria, Moraxella, Mycobacterium, Mycoplasma, Neisseria, Nocardia, Pasteurella, Pseudomonas, Rickettsia, Salmonella, Shigella, Spirillum, Staphylococcus, Streptobacillus, Streptococcus, Streptomyces, Treponema, Vibrio, Yersinia* and *Xanthomonas*. Specifically, the bacterial infection my be caused by a bacterium selected from the following species *Escherichia coli, Enterococcus faecalis, Mycobacterium aurum, Mycobacterium bovis, Mycobacterium fortuitum, Mycobacterium smegmatis, Pseudomonas aeruginosa, Staphylococcus aureus* and *Salmonella typhi*.

Alternatively, the infection may be a fungal infection caused by a fungus selected from, but not limited to, the group consisting of *Alternaria, Aspergillus, Candida, Cercospora, Cladosporium, Colletotrichum, Cryptococcus, Diplodia, Fusarium, Guignardia, Monilinia, Penicillium, Phytophthora, Plasmopara, Podosphaera, Puccinia, Pythium, Rhizoctonia, Rhizopus, Sclerotinia, Sphaerotheca, Trichoderma, Venturia* and *Verticillium*. Specifically, the fungal infection may be selected from the group of species consisting of *Aspergillus fumigatus, Aspergillus niger, Aspergillus parasiticus, Candida albicans, Colletotrichum gloeosporioides, Cryptococcus neoformans, Fusarium oxysporum, Penicillium digitum, Penicillium expansum, Penicillium italicum, Penicillium janthinellum, Trichoderma harzianum* and *Rhizoctonia solani*.

In a further embodiment the infection may be a helminthic infection caused by a helminth selected from, but not limited to, the group consisting of *Ascaris, Ancylostoma, Haemonchus, Trichostrongylos, Necator, Trichuris* and *Uncinaria*.

Plant Species Used in this Study

*Ptaeroxylon obliquum* was tested based on its reported biological activity, recorded antifungal activity, recorded medicinal uses, scientific research carried out to date and availability of plant material.

TABLE 1

Plant species used in this study

| Species (Family) | Common Name | Parts used | Voucher number | References |
|---|---|---|---|---|
| *Ptaeroxylon obliquum* (Thunb.) Radlk. (Ptaeroxylaceae) | Sneezewood | Leaves | PRU 96709 | UP Medicinal plant database, South Africa |

The plant leaves were collected from a tree growing on the Onderstepoort Campus of the University of Pretoria and authenticated by the HGW Schweikerd Herbarium of the University of Pretoria where a voucher specimen PRU 96079 is retained The plant material from this species was dried and ground to a fine powder (Ika Analytical Mill). This fine powder was then stored in brown bottles in a dark area, until all the extracts were prepared.

*Ptaeroxylon obliquum* (Thunb.) Radlk. (Family: Ptaeroxylaceae)

Botanical Description:

This is the only species of the genus *Ptaeroxylon* in Africa and varies in size from a shrub to a large tree of about 15 to 20 meters in height (Palmer and Pitman, 1972; Coates Palgrave, 1977; Van Wyk, 1995; Van Wyk et al., 2002). The bark becomes rough and flaky in old specimens, and is pale greyish-brown to dark grey. Leaves have up to eight pairs of leaflets, each of which are distinctly asymmetrical in shape (Van Wyk et al., 2002). The flowers are small, pale yellow, borne in dense clusters; and male and female flowers occur on different trees. The fruits are oblong capsules, each releasing two winged seeds when ripe (Palmer and Pitman, 1972; Coates Palgrave, 1977; Van Wyk, 1995; Van Wyk et al., 2002).

Medicinal Uses:

To relieve headache, the powdered wood is used as a snuff (Watt and Breyer-Brandwijk, 1962; Hutchings and Van Staden, 1994). The bark is used for the treatment of rheumatism and arthritis (Pujol, 1990). Infusions of the powdered wood are taken for the treatment of rheumatism and heart disease (Watt and Breyer-Brandwijk, 1962).

Preparation and Dosage:

Wood is powdered and used as a snuff, or decoctions and infusions of the wood or bark are taken (Watt and Breyer-Brandwijk, 1962; Pujol, 1990; Van Wyk et al., 2002).

Active Ingredients:

The leaves contain perforatin A (Van Wyk et al., 2002). The wood is chemically highly complex and contains numerous unusual chromones and other phenolic compounds. Examples are ptaeroxylone and umtatin (Dean and Taylor, 1966; Dictionary of Natural Products on CD-ROM, release 4:2, 1996; Van Wyk et al., 2002).

Pharmacological Effects:

Sneezing is induced presumably by the chromones in the wood. Perforatin A has antihypertensive effects (Van Wyk et al., 2002).

Distribution:

Sneezewood grows naturally along the eastern coastal parts of South Africa and northwards to the Northern Province (Von Breitenbach, 1986; Van Wyk et al., 2002).

The following examples are offered by way of illustration and not by way of limitation.

Example 1

In this example the inventors studied the anti-candidal activity of the selected eight plant species, by means of disc diffusion and serial microplate dilution assays as the methods of choice for screening.

Fungal Cultures

*Candida albicans* standard strain (ATCC 10231) and clinical isolates (obtained from the Department of Microbiology, National Health Laboratory Services, Pretoria, South Africa) were maintained on Sabouraud dextrose agar at 4° C. to prevent overgrowing and morphological changes.

Subcultures were freshly prepared before use. Inocula of the fungal cultures were prepared from the 24 h cultures.

Preparation of Inocula for Broth Micro-Dilution Assay

Inocula for use in the broth micro-dilution assay was prepared by transferring colonies from freshly prepared subcultures to Sabouraud dextrose broth until a turbidity of MacFarland Standard one was reached.

Extraction

Distilled water, acetone or hexane (Merck) were used as extractants. One gram of powdered plant material was extracted with 10 ml of appropriate solvent, lightly shaken, sonicated for 30 min and allowed to stand for 24 h in the refrigerator (4° C.). The extracts were then centrifuged at 4000×g for 15 minutes. The supernatant was retained and filtered through 0.22 µm syringe filters (Millipore). Extracts were stored at −18° C. to limit chemical decomposition. Yields of the extracts were determined gravimetrically using one milliliter (1 ml) of the extract (described in greater detail below):

Determination of Yields

Yields were determined gravimetrically:

1. Weigh glass dish.
2. Place 500 µl of the plant extract in the pre-weighed glass dish.
3. Dry extract overnight.
4. Weigh glass dish containing dry plant extract and calculate the difference. The difference is the yield per 500 µl of the plant extract.
5. Yields were determined in duplicate for each plant extract.

Disc Diffusion Assay

1. Three sterile filter paper discs (Whatmann, 10 mm) were impregnated with 200 µl of the respective plant extract on the first occasion and 300 µl on the second occasion.
2. These discs were dried to ensure that no solvent remained on the discs.
3. 23 ml of Mueller-Hinton Agar was poured in each Petri dish, on a completely horizontal surface to ensure that all plates were prepared in a standardized fashion.
4. 100 µl of the specific culture suspension (5×10$^5$ CFU/ml) was spread on the surface of each plate, which created a lawn of microbial growth.

5. The extract impregnated filter paper discs were placed on the inoculated Agar plates.
6. For positive control, antibiotic discs (amphotericin B, 10 µg (Mast diagnostics)) were placed on similarly inoculated plates. A negative control was prepared by using the respective solvent.
7. Plates were incubated at 37° C. for 24 h.
8. Antimicrobial activity was expressed as the mean diameter of the zone of inhibition (mm) around the disc and was measured at three places.
9. The assay was performed in duplicate.

Minimal Inhibitory Concentration Determination

Minimal inhibitory concentration (MIC) was evaluated on plant extracts that showed antimicrobial activity in the disc diffusion assay using the microplate dilution method developed by Eloff (1998b), with modifications for antifungal activity assay by Masoko et al. (2005). The serial microplate dilution method also allows for the testing of relatively large number of extracts simultaneously (Eloff, 1998b). MIC values were regarded as the lowest concentrations of the extract that inhibited the growth of *Candida albicans* standard strain (ATCC 10231) and clinical isolates. Total activity values were calculated as described by Eloff (2004). The total activity (ml) of the extracts was calculated as the total mass (mg) of the extract divided by the MIC value (mg/ml). Total activity value indicates the volume to which the extract can be diluted and still inhibit the growth of microbial cells (Eloff, 2004).

Minimal Inhibitory Concentration Assay

Preparation of Crude Plant Extracts

Distilled water, acetone or hexane (Merck) were used as extractants. Three grams (3 g) of powdered plant material was extracted with 30 ml of the appropriate solvent, lightly shaken, sonicated for 30 min and allowed to stand for 24 h in the refrigerator (4° C.). The extracts were then centrifuged at 4000×g for 15 min. The supernatant was retained and filtered through 0.45 µm and then through 0.22 µm syringe filters (Millipore); and decanted into pre-weighed labelled containers.

Hexane extracts were evaporated to dryness in an Air flow cabinet (Labotec, SA) overnight. Aqueous extracts were freeze-dried; and acetone extracts were stored at minus 18° C. to limit chemical decomposition.

Broth Micro-Dilution Assay

The assay was initiated by pouring sterile water aliquots (100 µl) into the wells of a 96-well microtitre plate. Exactly 100 µl of a 16 mg/ml plant extract (hexane, acetone or distilled water) was added in row A and mixed using a micropipette. From row A 100 µl was aspirated and added into row B and mixed. The procedure was repeated until all the wells were filled. An additional 100 µl in row H was discarded. 100 µl of *Candida albicans* standard strain (ATCC 10231) or clinical isolates (transferred to Sabouraud dextrose broth until a turbidity of MacFarlane Standard 1=4×10$^7$ CFU was reached) was added to the wells of the microtitre plate. 50 µl of a 0.2 mg/ml aqueous solution of p-iodonitro-tetrazolium violet (INT, Sigma) was added to each well. The plates were incubated at 35° C. for 24 h. Inhibition of microbial growth was indicated by the failure of the well to change colour; uninhibited growth was a pink colour. Amphotericin B was used as a positive control; acetone, hexane and distilled water were used as negative controls. The experiments were performed in triplicate and on two separate occasions.

Minimal Fungicidal Concentration Determination

The minimal fungicidal concentration (MFC) values were determined as the lowest concentration of the extract that inhibited 100 percent growth of *C. albicans* standard strain (ATCC 10231) and clinical isolates.

Minimal Fungicidal Concentration Assay

The assay was initiated by pouring fresh sterile water aliquots (100 μl) into the wells of a microtitre plate. Exactly 50 μl of the suspensions from the wells, which did not show any growth after incubation during MIC assays, were added to the wells. 50 μl of a 0.2 mg/ml aqueous solution of INT (Sigma) was added to each well. These suspensions were re-incubated at 35° C. for 24 h.

Minimal Inhibitory and Minimal Fungicidal Concentrations

The acetone and/or water extracts of all eight plant species showed anti-candidal activity against the *C. albicans* standard strain (ATCC 1023) and clinical isolates tested (Table 2 and 3). The antifungal compound, amphotericin B, inhibited the growth of all the strains tested (Table 4). Only the hexane extract of *Bidens pilosa* (whole plant) (MIC=2.00 mg/ml) showed anti-candidal activity against *C. albicans* standard strain (ATCC 10231). Although aqueous extracts inhibited *Candida* growth, the acetone extracts had the lowest MIC values. However, the effectively of the water extracts is worth noting since traditional medicine in South Africa is mainly prepared as decoctions, infusions, syrups or tinctures, taken orally (Van Wyk et al., 2002; Van Wyk et al., 2009).

Inhibition at concentrations <1 mg/ml, against the *C. albicans* strains tested, was observed for the acetone extracts of *B. pilosa* (whole plant), *H. caffrum* (leaves), *P. obliquum* (leaves), *R. melanophloeos* (leaves) and *S. birrea* (stem bark) as well as the aqueous extracts of *B. pilosa* (whole plant) and *S. birrea* (stem bark) (Table 2). Motsei at al. (2003) found much less activity with *B. pilosa* aqueous extract against *C. albicans* clinical isolates from a 5-month-old baby (25 mg/ml) and an adult (25 mg/ml), and a standard strain of *C. albicans* ATCC 10231 (25 mg/ml).

Previous findings for antifungal activity of the plants tested in this study, confirming the results, have been reported for the aqueous extracts of *Z. mucronata* stem-bark (Gundiza, 1986), *S. longepedunculata* root (Desta, 1993), *H. caffrum* bark (Buwa and Van Staden, 2006), methanolic/ethanolic extracts of *S. birrea* root/stem-bark (Eloff, 2001; Hamza et al., 2006; Runyoro et al., 2006). No antifungal activity has previously been reported for the extracts of *R. melanophloeos* (Hamza et al., 2006, Steenkamp et al., 2007), which may explain the weak activity evidenced in this study.

TABLE 2

Minimal inhibitory concentrations for the plant extracts investigated

| | | | \*MIC (mg/ml) *Candida albicans* | | | | | | |
|---|---|---|---|---|---|---|---|---|---|
| | | | ATCC | Clinical isolates | | | | | |
| Plant | Plant part | Solvent | 10231 | M0824 | M0825 | M0826 | 1051604 | 1051608 | 1051255 |
| *Bidens pilosa* | Whole plant | Water | 1.5 | 0.5 | 2 | 0.5 | 0.23 | 0.25 | 2 |
| | | Acetone | 2 | 1.25 | 2 | 0.5 | 0.62 | 0.25 | 2 |
| | | Hexane | 2 | nd | nd | nd | nd | nd | nd |
| *Dichrostachys cinerea* | Stem bark | Water | nd | nd | nd | nd | nd | nd | nd |
| | | Acetone | 4 | nd | nd | nd | nd | nd | nd |
| | | Hexane | nd | nd | nd | nd | nd | nd | nd |
| *Harpephyllum caffrum* | Leaves | Water | 2 | 2 | 2 | 2 | 2 | 2 | 2 |
| | | Acetone | 1 | 2 | 1 | 0.5 | 0.5 | 0.5 | 1 |
| *Ptaeroxylon obliquum* | Leaves | Water | 2 | 2 | 2 | 2 | 2 | 2 | 2 |
| | | Acetone | 0.5 | 0.5 | 0.5 | 0.5 | 0.5 | 0.5 | 0.5 |
| *Rapanea melanophloeos* | Leaves | Water | 2 | 2 | 2 | 2 | 1 | 2 | 2 |
| | | Acetone | 2 | 1 | 2 | 0.5 | 1 | 2 | 2 |
| *Sclerocarya birrea* | Stem bark | Water | 3 | 1.25 | 2 | 0.5 | 1.25 | 0.5 | 2 |
| | | Acetone | 0.25 | 1.25 | 0.13 | 0.5 | 0.75 | 0.13 | 0.13 |
| | | Hexane | nd | nd | nd | nd | nd | nd | nd |
| | Leaves | Water | >2.00 | >2.00 | >2.00 | >2.00 | >2.00 | >2.00 | >2.00 |
| | | Acetone | 1.5 | 1.5 | 0.75 | 2 | 2 | >2.00 | 2 |
| *Securidaca longepedunculata* | Root bark | Water | nd | nd | nd | nd | nd | nd | nd |
| | | Acetone | 4 | nd | nd | nd | nd | nd | nd |
| | | Hexane | nd | nd | nd | nd | nd | nd | nd |
| *Ziziphus mucronata* | Root bark | Water | 4 | nd | nd | nd | nd | nd | nd |
| | | Acetone | 4 | nd | nd | nd | nd | nd | nd |
| | | Hexane | nd | nd | nd | nd | nd | nd | nd |

\*MIC: Minimal inhibitory concentration representing the mean value
nd: MIC not determined since the crude plant extract had such a high MIC with ATCC 10231 and showed no zone of inhibition when using the disc-diffusion assay

TABLE 3

Minimal fungicidal concentrations for the plant extracts investigated

| | | | \*MFC (mg/ml) *Candida albicans* | | | | | | |
|---|---|---|---|---|---|---|---|---|---|
| | | | ATCC | Clinical isolates | | | | | |
| Plant | Plant part | Solvent | 10231 | M0824 | M0825 | M0826 | 1051604 | 1051608 | 1051255 |
| *Bidens pilosa* | Whole plant | Water | 2 | 1 | 2 | 1 | 1 | 1 | 2 |
| | | Acetone | 2 | 2 | 2 | 1 | 1 | 1 | 2 |
| | | Hexane | 2 | nd | nd | nd | nd | nd | nd |

TABLE 3-continued

Minimal fungicidal concentrations for the plant extracts investigated

|  |  |  | *MFC (mg/ml) Candida albicans | | | | | | |
|---|---|---|---|---|---|---|---|---|---|
|  | Plant |  | ATCC | Clinical isolates | | | | | |
| Plant | part | Solvent | 10231 | M0824 | M0825 | M0826 | 1051604 | 1051608 | 1051255 |
| Dichrostachys cinerea | Stem bark | Water | nd | nd | nd | nd | nd | nd | nd |
|  |  | Acetone | 4 | nd | nd | nd | nd | nd | nd |
|  |  | Hexane | nd | nd | nd | nd | nd | nd | nd |
| Harpephyllum caffrum | Leaves | Water | 2 | 2 | 2 | 2 | 2 | 2 | 2 |
|  |  | Acetone | 2 | 2 | 2 | 0.5 | 0.5 | 0.5 | 2 |
| Ptaeroxylon obliquum | Leaves | Water | 2 | 2 | 2 | 2 | 2 | 2 | 2 |
|  |  | Acetone | 1 | 0.5 | 1 | 0.5 | 0.5 | 0.5 | 1 |
| Rapanea melanophloeos | Leaves | Water | 2 | 2 | 2 | 2 | 1 | 2 | 2 |
|  |  | Acetone | 2 | 1 | 2 | 0.5 | 1 | 2 | 2 |
| Sclerocarya birrea | Stem bark | Water | 3 | 4 | 2 | 1 | 2 | 1 | 2 |
|  |  | Acetone | 2.12 | 4 | 0.5 | 1 | 2 | 1 | 0.5 |
|  |  | Hexane | nd | nd | nd | nd | nd | nd | nd |
|  | Leaves | Water | >2.00 | >2.00 | >2.00 | >2.00 | >2.00 | >2.00 | >2.00 |
|  |  | Acetone | 1.5 | 1.5 | 0.75 | 2 | 2 | >2.00 | 2 |
| Securidaca longepedunculata | Root bark | Water | nd | nd | nd | nd | nd | nd | nd |
|  |  | Acetone | 4 | nd | nd | nd | nd | nd | nd |
|  |  | Hexane | nd | nd | nd | nd | nd | nd | nd |
| Ziziphus mucronata | Root bark | Water | 4 | nd | nd | nd | nd | nd | nd |
|  |  | Acetone | 4 | nd | nd | nd | nd | nd | nd |
|  |  | Hexane | nd | nd | nd | nd | nd | nd | nd |

*MFC: Minimal fungicidal concentration representing the mean value
nd: MFC not determined; no antimicrobial activity was present

TABLE 4

Minimal inhibitory and minimal fungicidal concentrations for Amphotericin B

|  | Candida albicans | | | | | | |
|---|---|---|---|---|---|---|---|
|  | ATCC | Clinical isolates | | | | | |
|  | 10231 | M0824 | M0825 | M0826 | 1051604 | 1051608 | 1051255 |
| *MIC (mg/ml) | 0.11 | 0.03 | 0.03 | 0.06 | 0.06 | 0.11 | 0.03 |
| *MFC (mg/ml) | 0.11 | 0.11 | 0.06 | 0.11 | 0.06 | 0.11 | 0.23 |

*MIC: Minimal Inhibitory concentration representing the mean value
*MFC: Minimal fungicidal concentration representing the mean value

TABLE 5

Total activity values (ml/g) for the plant extracts investigated against
Candida albicans standard strain (ATCC 10231) and six clinical isolates

|  |  |  | Total activity values (ml/mg) | | | | | | |
|---|---|---|---|---|---|---|---|---|---|
|  | Plant |  | ATCC | Clinical isolates | | | | | |
| Plant | part | Solvent | 10231 | M0824 | M0825 | M0826 | 1051604 | 1051608 | 1051255 |
| Bidens pilosa | Whole plant | Water | 126 | 379 | 95 | 379 | 824 | 758 | 95 |
|  |  | Acetone | 12 | 18 | 12 | 46 | 37 | 92 | 12 |
|  |  | Hexane | 14 | — | — | — | — | — | — |
| Dichrostachys cinerea | Stem bark | Acetone | 51 | — | — | — | — | — | — |
| Harpephyllum caffrum | Leaves | Water | 92 | 92 | 92 | 92 | 92 | 92 | 92 |
|  |  | Acetone | 143 | 71 | 143 | 286 | 286 | 286 | 143 |
| Ptaeroxylon obliquum | Leaves | Water | 119 | 119 | 119 | 119 | 119 | 119 | 119 |
|  |  | Acetone | 323 | 323 | 323 | 323 | 323 | 323 | 323 |
| Rapanea | Leaves | Water | 127 | 127 | 127 | 127 | 255 | 127 | 127 |

TABLE 5-continued

Total activity values (ml/g) for the plant extracts investigated against
*Candida albicans* standard strain (ATCC 10231) and six clinical isolates

| | | | Total activity values (ml/mg) | | | | | | |
|---|---|---|---|---|---|---|---|---|---|
| | | | ATCC | Clinical isolates | | | | | |
| Plant | Plant part | Solvent | 10231 | M0824 | M0825 | M0826 | 1051604 | 1051608 | 1051255 |
| melanophloeos | | Acetone | 70 | 140 | 70 | 280 | 140 | 70 | 70 |
| Sclerocarya | Stem | Water | 44 | 107 | 67 | 266 | 107 | 266 | 67 |
| birrea | bark | Acetone | 158 | 32 | 304 | 79 | 53 | 304 | 304 |
| | Leaves | Water | 68 | 68 | 68 | 68 | 68 | 68 | 68 |
| | | Acetone | 17 | 17 | 33 | 13 | 13 | 13 | 13 |
| Securidaca longepedunculata | Root bark | Acetone | 7 | — | — | — | — | — | — |
| Ziziphus mucronata | Root bark | Water | 22 | — | — | — | — | — | — |
| | | Acetone | 11 | — | — | — | — | — | — |

All the plant species examined had some activity against the fungal test organisms in this study. *H. caffrum, P. obliquum, R. melanophloeos* and *S. birrea* were the most active of the plant species tested against *C. albicans* standard strain (ATCC 10231) and clinical isolates. These results also imply that the extracts contain compounds with therapeutic potential against *C. albicans*, *D. cinerea*, *S. longepedunculata* and *Z. mucronata* extracts were the least sensitive against the fungal test organisms. The stem bark of *S. birrea* resulted in lower MIC values compared to the leaves (Table 2).

Following the finding that *H. caffrum* (leaves), *P. obliquum* (leaves), *R. melanophloeos* (leaves) and *S. birrea* (stem bark) had the lowest MIC values against *C. albicans* standard strain (ATCC 10231) and clinical isolates tested, the next step involved bioautography analysis from the acetone extracts of these species.

Example 2

Bioautography is regarded as the most efficient method for activity-guided isolation of components (Hostettmann et al., 2000). Bioautography combines thin layer chromatography (TLC) with a bioassay in situ and allows the localization of the active compounds in a complex plant extract (Shai, 2007). Cultures of bacteria or fungi are sprayed on developed TLC plates from which the eluents have been removed and incubated for a specific duration in humid chambers. Zones of inhibition are visualized by the detection of dehydrogenase activity with a tetrazolium salt. A reference chromatogram stained with a suitable reagent provides information about the nature of the active component, such as relative polarity (Shai, 2007).

In this example the inventors identified the active compounds in the most active acetone plant extracts identified after MIC and MFC (See Example 1, above) namely: *Harpephyllum caffrum* (leaves); *Ptaeroxylon obliquum* (leaves); *Rapanea melanophloeos* (leaves) and *Sclerocarya birrea* (stem bark).

Bioautography Procedure

For bioautography analysis thin layer chromatography (TLC) plates (10×10 cm) were loaded with 10 µl (10 mg/ml) of the extracts and eluted in the three different mobile eluting solvent systems of varying polarity: developed in the Phytomedicine Programme Laboratory, namely: ethyl acetate/methanol/water [EMW] [10:1.35:1](polar/neutral); chloroform/ethyl acetate/formic acid [CEF] [10:8:2](intermediate polarity/acidic); benzene/ethanol/ammonia [BEA] [18:2:0.2](non-polar/basic) (Kotze and Eloff, 2002). Duplicate TLC plates were visualized under ultraviolet (UV) light (366 nm) and sprayed with vanillin spray reagent (0.1 g vanillin dissolved in 28 ml methanol and 1 ml sulphuric acid added) and served as reference plates (FIG. 1).

The chromatograms were dried for 5 days at room temperature to remove the eluent solvent systems. Developed TLC plates were sprayed with a concentrated suspension of the test organism (*C. albicans* standard strain (ATCC 10231) and clinical isolates) prepared in Sabouraud dextrose broth in a Biosafety Class II cabinet (Labotec, SA). The sprayed plates were placed in a humid chamber (100 percent relative humidity) and incubated overnight at 25° C. Plates were then sprayed with a 2 mg/ml p-iodonitro-tetrazolium violet (INT, Sigma) solution and further incubated at 25° C. until a purple-red colour change was evident. Plates with white spots at bands where reduction of INT to formazan did not occur, were tightly sealed in transparent plastic bags and retardation factor ($R_f$) values of inhibitory zones recorded.

The bioautography procedure was repeated on three separate occasions.

The compounds whose retardation factor ($R_f$) values are listed in Table 6 were identified as the active constituents that displayed growth inhibition of *C. albicans* standard strain (ATCC 10231) and clinical isolates tested. The acetone extracts of *H. caffrum* and *R. melanophloeos* leaves had no visible activity against *C. albicans* standard strain and/or clinical isolates tested as evidenced by the absence of clear zones on TLC bioautograms (FIG. 2).

Figure 2:
FIG. 2: TLC Bioautograms

The acetone extracts of *P. obliquum* had the highest number of active compounds against the opportunistic pathogen *C. albicans* and clinical isolates (FIG. 2). The active components in the acetone extract of the leaves of *P. obliquum* range from non-polar to intermediate polarity in nature.

TABLE 6

The $R_f$ values of active compounds from acetone leaf and stem bark extracts of different plant species against *C. albicans* standard strain and six clinical isolates

| Plant species | Plant part | Eluting solvent system | Candida albicans ATCC 10231 | Clinical isolates M0824 | M0825 | M0826 | 1051604 | 1051608 | 1051255 |
|---|---|---|---|---|---|---|---|---|---|
| Harpephyllum caffrum | Leaves | EMW | — | — | — | — | — | — | — |
| | | CEF | — | — | — | — | — | — | — |
| | | BEA | — | — | — | — | — | — | — |
| Ptaeroxylon obliquum | Leaves | EMW | — | — | — | — | — | — | 0.88 |
| | | CEF | 0.88 | — | — | — | — | 0.88 | 0.83 |
| | | | 0.66 | — | — | 0.65 | — | 0.68 | 0.60 |
| | | BEA | — | — | — | — | — | — | — |
| Rapanea melanophloeos | Leaves | EMW | — | — | — | — | — | — | — |
| | | CEF | — | — | — | — | — | — | — |
| | | BEA | — | — | — | — | — | — | — |
| Sclerocarya birrea | Stem bark | EMW | — | 0.06 | — | — | — | 0.02 | — |
| | | CEF | 0.04 | — | — | 0.03 | — | — | 0.17 |
| | | BEA | — | 0.05 | — | — | — | 0.05 | 0.05 |

$R_f$: retardation factor
EMW: ethyl acetate/methanol/water
CEF: chloroform/ethyl acetate/formic acid
BEA: benzene/ethanol/ammonia
—: no visible activity Bioassay-guided isolation has resulted in the identification of the responsible antifungal agents in *S. birrea*. These include procyanidins (Galvez et al., 1993; Van Wyk et al., 2009), gallotannins and catechins (Watt and Breyer-Brandwijk, 1962; Iwu, 1993; Van Wyk et al., 2009). Bark yields 3.5-20.5 percent tannin, 10.7 percent tanning matter and traces of alkaloids (Watt and Breyer-Brandwijk, 1962; Eloff 2001). Chemical constituents of *P. obliquum* are poorly known, but the presence of unusual chromones and other phenolic compounds (such as ptaeroxylone and umtatin) in the wood (Dean and Taylor, 1966; Dictionary of Natural Products, 2008; Van Wyk et al., 2009) and perforatin A from the leaves have been reported. Perforatin A has antihypertensive effects (Langenhoven et al., 1988; Van Wyk et al., 2009). *H. caffrum* contains a large amount of phenolic compounds which are reported to be responsible for the antifungal activity (El Sherbeiny and El Ansari, 1976). From the leaves of *R. melanophloeos*, saponins such as sakurasosaponin have been isolated which contain antifungal activity (Ohtani et al., 1993).

The results indicate that *P. obliquum* had the highest number of active compounds against the fungal test organisms. *S. birrea* had the second highest number of active compounds against the fungal test organisms. These results correlate with the MIC and MFC values (Tables 2 and 3) where *P. obliquum* had lower MIC values against the fungal test organisms compared to *S. birrea*, *H. caffrum* and *R. melanophloeos* had no visible activity against the fungal test organisms as evidenced by the absence of clear zones on TLC bioautograms. These extracts were also less sensitive against the fungal test organisms. (Tables 2 and 3) compared to *P. obliquum* and *S. birrea* with MIC values ranging between 1.00 mg/ml to 2.00 mg/ml. The fact that no zones of inhibition were encountered although there was some activity in the extracts may possible be due to volatility of the active compound(s) or to synergism between different compounds that are not active once separated.

Some medicinal plants contain free radical scavengers such as polyphenols, flavonoids and phenolic compounds (Khalaf et. al., 2008) and these antioxidants may reduce oxidative stress, thereby stimulating the immune process. Although *H. caffrum* and *R. melanophloeos* extracts did not have any active compounds by bioautography and have been used traditionally to treat infections.

Example 3

Antioxidant Activity

Antioxidants are substances which have the capability to neutralize free radicals (superoxide, hydroxyl radicals and nitric oxide) and other reactive species (hydrogen peroxide, hypochloric acid and proxynitrite) produced during aerobic metabolism in the body that can cause oxidative damage of amino acids, lipids, proteins and DNA (Iuliano et al., 1997; Fang et al., 2002; Vimal et al., 2009). Free radicals have the ability to react with and damage many structures in the body and are involved in various related physiological processes and diseases such as ageing, cancer and artherosclerosis (Fikel and Holbrook, 2000; Senthil et al., 2004; Rackova et al., 2007; Vimal et al., 2009).

Natural antioxidants of plant origin are responsible for inhibiting or preventing the deleterious consequences of oxidative stress (Khalaf et al., 2008). Medicinal plants contain free radical scavengers such as polyphenols, flavonoids and phenolic compounds (Khalaf et al., 2008), and may be used as nutraceuticals and phytoceuticals as they have significant impact on the status of human health and disease prevention (Noguchi and Nikki, 2000; Vimal et al., 2009).

In this example the inventors investigated the antioxidant activity in acetone plant extracts of *Harpephyllum caffrum* (leaves); *Ptaeroxylon obliquum* (leaves); *Rapanea melanophloeos* (leaves) and *Sclerocarya birrea* (stem bark).

Qualitative Evaluation

The qualitative antioxidant activity of selected plant species was carried out using the method of Deby and Margotteaux (1970). Thin layer chromatography (TLC) plates (10× 10 cm) were loaded with 10 µl (10 mg/ml) of the extracts and eluted in the three different mobile eluting solvent systems of varying polarity, developed in the Phytomedicine Programme Laboratory, namely: ethyl acetate/methanol/water [EMW] [10:1.35:1](polar/neutral); chloroform/ethyl acetate/formic acid [CEF] [10:8:2](intermediate polarity/acidic); benzene/ethanol/ammonia [BEA] [18:2:0.2](non-polar/basic) (Kotze and Eloff, 2002).

For the determination of antioxidant activity, developed TLC plates were sprayed with 0.2% 1-1-diphenyl-2-picryl-hydrazyl (DPPH) (Sigma®) in methanol as indicator. A positive reaction was indicated by the appearance of a yellow spot against a purple background.

Figure 3:
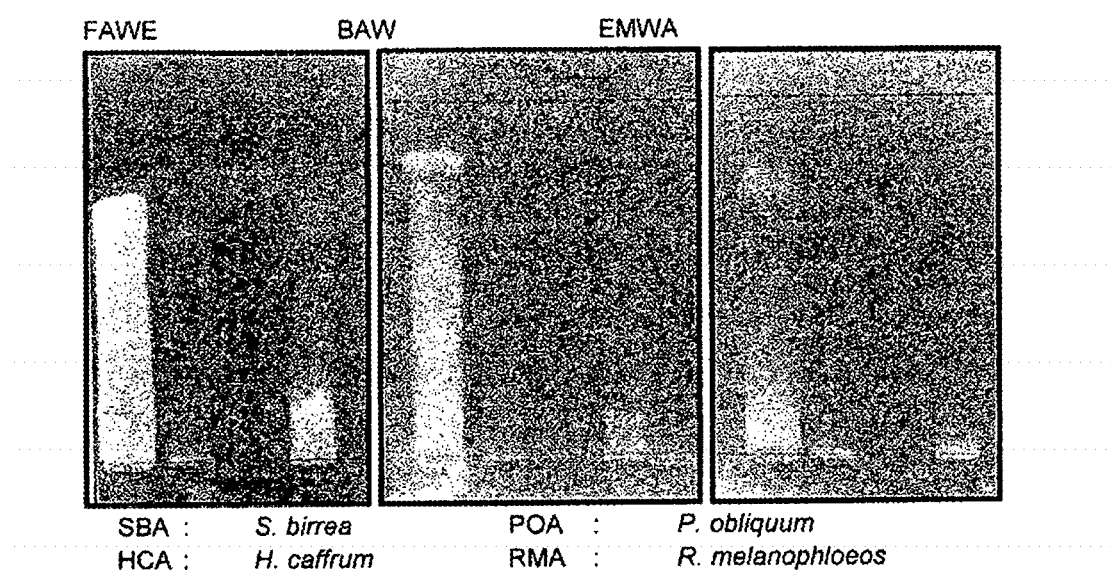
FIG. 3: Antioxidant activity of *H. caffrum, P. obliquum, R. melanophloeos* and *S. birrea*

All the plant extracts tested showed antioxidant activity when eluted in the three different mobile eluting solvent systems. The acetone stem bark extract of S. birrea showed the highest antioxidant activity when eluted in the three different mobile eluting solvent systems. The antioxidant compounds present in extracts of H. caffrum, P. obliquum and R. melanophloeos did not move from the base (FIG. 3).

To make the antioxidant activity of H. caffrum, P. obliquum and R. melanophloeos move from the base (FIG. 3); three different mobile eluting solvent systems were used as those described above. These mobile eluting solvent systems are also developed in the Phytomedicine Programme Laboratory, namely: ethyl acetate/methanol/water/acetic acid [EMWA] [10:1.35:1:2.5](polar/neutral) ethyl acetate/water/formic acid/acetic acid [FAWE] [70:20:3:2] (polar/neutral) and butanol/acetic acid/water [BAW] [4:1:5] (polar/neutral) (Kotze and Eloff, 2002).

DPPH Radical Scavenging Activity

The effect of the extracts on the DPPH radical was estimated using the method of Liyana-Pathirana and Shahidi (2005), with minor modifications. A solution of 0.135 mM DPPH in methanol was prepared and 185 µl of this solution was mixed with 15 µl of varying concentrations of the extract in a 96-well plate. After 15 min of incubation in the dark, the absorbance of the mixture was determined at 570 nm using a microplate reader. Trolox was used as the reference antioxidant compound and the result expressed as Trolox equivalence (TE). TE is defined as the ratio of the sample slope to the standard slope and is thus unitless.

TEAC Assay

The assay was performed according to the method of Re et al. (1999), with minor modifications. The assay involves the production of the ABTS$^+$ through the reaction between 7 mM ABTS in water and 2.45 mM potassium persulfate, which is stored in the dark for at least 16 h at 4° C. Into a 96-well plate was pipetted: 20 µl standard or sample at varying concentrations and 200 µl ABTS$^+$. The absorbance of the mixture was determined at 405 nm using a microplate reader. Trolox was used as the reference antioxidant compound and the result expressed as Trolox equivalence (TE)

Determination of Total Flavonoids

Total flavonoid content was determined using the method of Ordonez et al. (2006), with modifications. Into a 96-well plate was pipetted: 20 µl of the standard (rutin) or sample, 20 µl sodium nitrate (3%), 20 µl aluminium trichloride (1%) and 100 µl 2M sodium hydroxide. Sample (20 µl) and 140 µl water served as background control to eliminate phytochemical absorbance interference. The absorbance was measured at 570 nm (Hewlett Packard UV-VIS spectrophotometer). Total flavonoid content was calculated as rutin equivalence (mg/g).

Determination of Total Phenolics

Total phenolic content was determined using the modified Folin-Ciocalteu method of Wolfe et al. (2003). Into a 96-well plate was pipetted: 20 µl standard (gallic acid) or sample, 60 µl 0.3M Folin-Ciocalteu reagent and 100 µl 3% sodium carbonate. The mixture was incubated for 2 h. The absorbance was measured at 630 nm (Hewlett Packard UV-VIS spectrophotometer). Total phenolic content is expressed as mg/g gallic acid equivalence DPPH Radical Scavenging Activity, TEAC Assay, Determination of Total Flavonoids and Total Phenolics S. birrea had the highest antioxidant activity of the four plant species tested (Table 7). High antioxidant activity has previously been reported for this plant by other authors (Masoko et al., 2008; Moya et al., 2010). Polyphenols and flavonoids are said to be responsible for the antioxidant activity in S. birrea (Braca et al., 2003). This activity may be ascribed to the high polyphenolic content detected in the extracts (Table 8).

TABLE 7

Antioxidant and polyphenolic content of the plants containing significant antifungal activity

| Plant | Antioxidant activity | | Polyphenolic content | |
|---|---|---|---|---|
| | DPPH$^a$ | TEAC$^a$ | TPC$^b$ | TFC$^c$ |
| S. birrea | 1.23 ± 0.03 | 1.05 ± 0.08 | 4.05 ± 0.76 | 36.08 ± 1.47 |
| H. caffrum | 0.22 ± 0.01 | 0.33 ± 0.02 | 0.65 ± 0.05 | 14.88 ± 0.66 |
| R. melanophloeos | 0.03 ± 0.00 | 0.06 ± 0.00 | 0.27 ± 0.01 | 5.88 ± 0.24 |
| P. obliquum | 0.02 ± 0.00 | 0.03 ± 0.00 | 0.48 ± 0.04 | 5.11 ± 0.41 |

$^a$Trolox equivalence
$^b$Gallic acid equivalence (mg/g)
$^c$Rutin equivalence (mg/g)

Chemical constituents of H. caffrum are poorly known, but the presence of polyphenolic compounds and flavonoids have been reported. These include organic acids, such as protocatechuic acid, and flavonols such as Kaempferol (El Sherbeiny and El Ansari, 1976; Van Wyk et al., 2009). The responsible antioxidant agents in P. obliquum and R. melanophloeos are not known. No antibacterial compounds were detected in the bioautography of the H. caffrum extract. The fact that H. caffrum extracts had the second highest anti-oxidant activity may explain the traditional use to combat infection indirectly via stimulating the host immune response and not by a direct antibacterial effect.

All four plant species tested contained compounds have antioxidant activity, as well as anti-candidal compounds (Tables 2 and 3). In order to develop a natural product that can protect users against oral Candida infections, it is therefore of utmost importance to test the safety of plant extracts. Testing of the cytotoxicity of plant extracts involves exposure of human or mammalian cells to specified concentrations of the test substances or mixture. After incubation for specific periods, the cells viability is determined using various methods. Therefore, the next step involved determining the cytotoxicity of dried acetone extracts of H. caffrum, P. obliquum, R. melanophloeos and S. birrea reconstituted in dimethyl sulphoxide (DMSO) against mouse fibroblast cells.

Example 4

Cytotoxicity

Users of traditional medicines accept that these preparations are safe for human consumption and that medicinal plants are "pure and natural" which equates to harmless (Street et al., 2008). Some plants have chemical defenses enabling them to deter, stun, poison or kill threatening species, therefore one cannot assume that plant extracts are inevitably safe (Gurib-Fakim, 2006). Some plants used for medicinal purposes or as food are potentially toxic, mutagenic and carcinogenic (Schimmer et al., 1988; Higashimoto at al., 1993; Kassie at al., 1996).

Misidentification of plant species, poor quality of the preparations, prolonged usage and addition of toxic substances to plant derived remedies contribute significantly to the toxicity associated with plant extracts (Stewart and Steenkamp, 2000; Wolpert, 2001; Fennell et al., 2004). It is therefore of utmost importance to test the safety of plant extracts. Testing of the cytotoxicity of plant extracts and the isolated compounds involves exposure of human or mammalian cells to specified concentrations of the test substance or mixture. After incubation for specific periods the cell viability is determined using various methods (Mosmann, 1983).

In this example the inventors investigated the cytotoxicity of dried acetone extracts of *Harpephyllum caffrum* (leaves); *Ptaeroxylon obliquum* (leaves); *Rapanea melanophloeos* (leaves) and *Sclerocarya birrea* (stem bark) using the MTT [3-(4.5-dimethylthiazolyl)2.5-diphenyltetrazolium bromide] reduction assay.

MTT Assay

The MTT assay was used to determine the cytotoxicity of dried acetone extracts of *H. caffrum* (leaves); *P. obliquum* (leaves); *R. melanophloeos* (leaves) and *S. birrea* (stem bark) reconstituted in dimethyl sulphoxide (DMSO) against Mouse fibroblast cells (obtained from the Department of Plant Science, Faculty of Natural and Agricultural Sciences, University of Pretoria, South Africa).

The MTT assay is widely used for measuring cell proliferation and cytotoxicity (Shai, 2007). MTT (yellow) is reduced into a formazan (purple) by viable cells. The colour intensity of the formazan produced, which is directly proportional to the number of viable cells, is measured using a spectrophotometer (Mosmann, 1983; Shai, 2007).

Cells were maintained in minimal essential medium (MEM) (Highveld Biological, South Africa) supplemented with 0.1% gentamicin (Virbac) and 5% foetal calf serum (Adcock-Ingram). Cultures for the assay were prepared from confluent monolayer cells and seeded at a density of $1 \times 10^4$ cells per ml in a 96 well microtitre plate and incubated overnight at 37° C. in a 5% $CO_2$ atmosphere. Dried crude plant extracts (100 mg) were reconstituted in 1 ml of DMSO and serial 10-fold dilutions of each extract were prepared in growth medium. The growth medium on sub-confluent monolayer cells grown overnight in microtitre plates was removed and cells were exposed to 200 µl of the extracts at different concentrations and incubated again at 37° C. for 5 days. Viability of cells was determined using the tetrazolium-based colorimetric assay (MTT assay) described by Mossmann (1983). Before the addition of MTT, the extract-containing medium on the cells was replaced with fresh culture medium to exclude reduction of the tetrazolium compound by plant extracts. The assay is based on mitochondrial dehydrogenase activity which is assessed by the reductive cleavage of the tetrazolium salt MTT [3-(4.5-dimethylthiazolyl)2.5-diphenyltetrazolium bromide] due to the succinic dehydrogenase present in living cells to yield a purple formazan dye. The cells were incubated with 30 µl of 5 mg/ml MTT in phosphate-buffered saline (PBS) for four hours. Thereafter, medium was removed and cells washed with PBS. DMSO (50 µl) was added to the cells and absorbance was measured using a Versamax microplate reader at 570 nm. Berberine chloride (Sigma) was used as a positive control, wells containing only cells acted as the negative control and a solvent control was also included. The percentage cell viability following the addition of varying concentrations of the extracts in relation to controls was calculated. The $LC_{50}$ values were calculated (using SoftMax Pro4.8 Software) as the concentration of plant extracts resulting in 50 percent reduction of absorbance compared to untreated cells. Tests were carried out in quadruplicate and each experiment was repeated three times.

Figure 4:
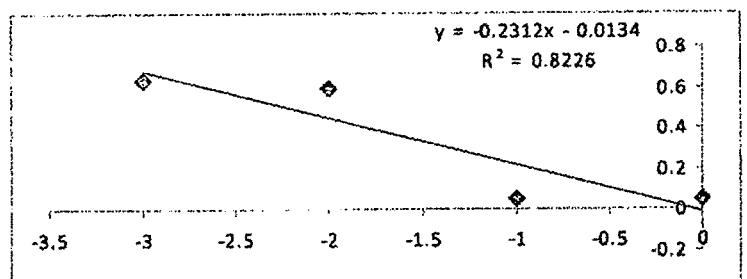
FIG. 4: Cytotoxicity of *P. obliquum* ($LC_{50}$=35.58 μg/ml) against mouse fibroblast cells
Figure 5:
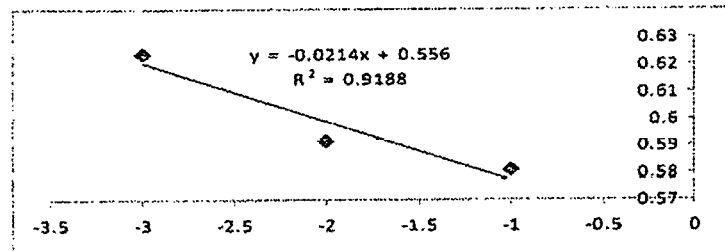
FIG. 5: Cytotoxicity of berberine ($LC_{50}$=9.04 μg/ml) against mouse fibroblast cells
Figure 7:
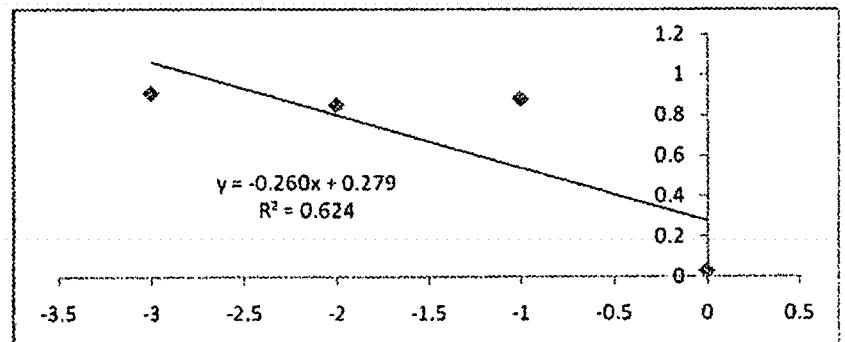
FIG. 7: Cytotoxicity of the hexane-fraction ($LC_{50}$=211.99 μg/ml) against mouse fibroblast cells
Figure 8:
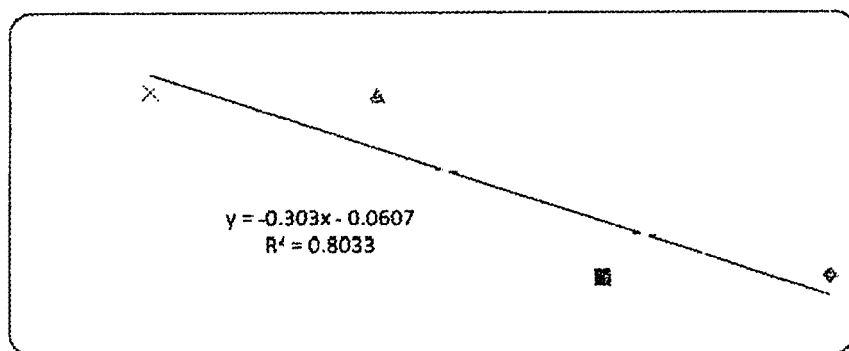
FIG. 8: Cytotoxicity of the chloroform-fraction ($LC_{50}$=28.64 μg/ml) against mouse fibroblast cells
Figure 9:
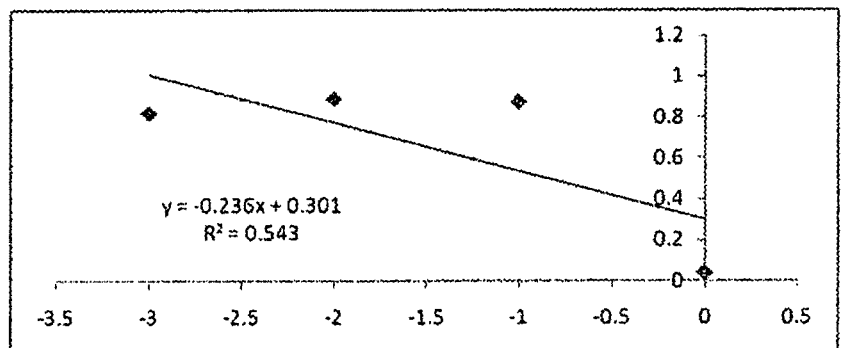
FIG. 9: Cytotoxicity of the $ETAC_1$-fraction ($LC_{50}$=229.69 μg/ml) against mouse fibroblast cells
Figure 10:
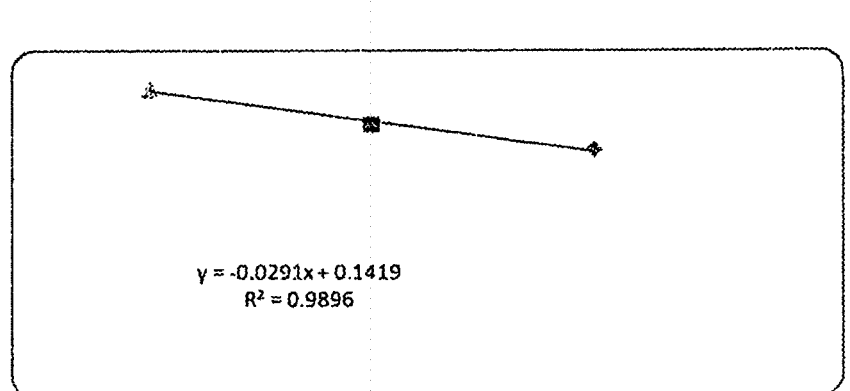
FIG. 10: Cytotoxicity of the $H_2O$-fraction ($LC_{50}$=0.08 μg/ml) against mouse fibroblast cells
Figure 11:
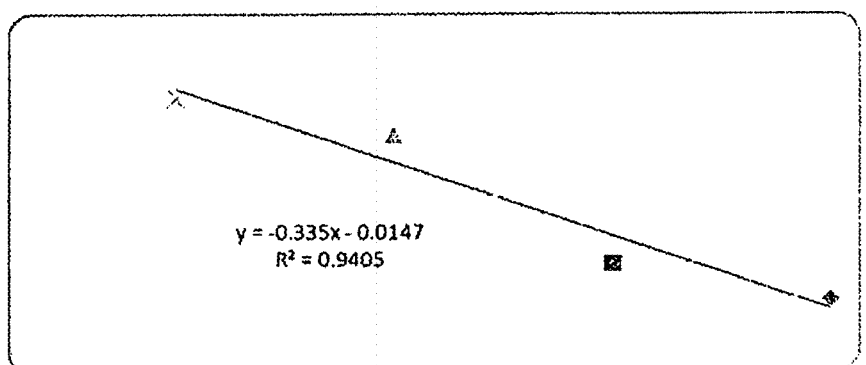
FIG. 11: Cytotoxicity of the $ETAC_2$-fraction ($LC_{50}$=39.69 μg/ml) against mouse fibroblast cells
Figure 12:
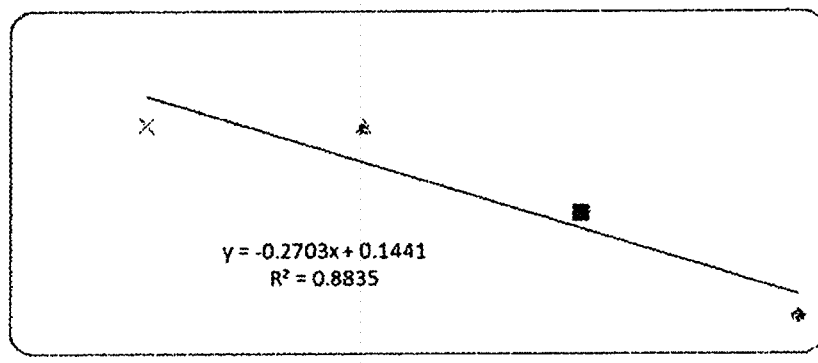
FIG. 12: Cytotoxicity of the $ETAC_{21}$-fraction ($LC_{50}$=71.27 μg/ml) against mouse fibroblast cells

The cytotoxicity of dried acetone extracts of *H. caffrum* (leaves); *P. obliquum* (leaves); *R. melanophloeos* (leaves) and *S. birrea* (stem bark) was determined against mouse fibroblast cells using the MTT assay. The results are presented in FIGS. 5, 6, 7 and 8. Berberine was used as a positive control and was found to be toxic with a $LC_{60}$ of 9.04 µg/ml (FIG. 5). *H. caffrum* was more toxic than Berberine, with a $LC_{50}$ of 2.07 µg/ml (FIG. 5). *P. obliquum*, with a $LC_{50}$ of 35.58 µg/ml (FIG. 4), was less toxic than Berberine and *H. caffrum* but more toxic than *R. melanophloeos* ($LC_{50}$=434.50 µg/ml) (FIG. 7) and *S. birrea* ($LC_{50}$>1000 µg/ml) (FIG. 8). *S. birrea* has been reported to have cytotoxic effects in Vero cells (McGaw et al., 2007) and to reduce cell viability in renal epithelial cell lines (Gondwe et al., 2008). No reports regarding cytotoxicity could be obtained for the other plant extracts investigated.

Selective activity of the extracts was calculated as follows:

$$\text{Selectivity index (SI)} = LC_{50} \text{ against mouse fibroblast cells/MIC}$$

The selectivity index is calculated to determine the relationship of activity of a test product to its cytotoxic concentration. The higher the number, the better the product. The selectivity index obtained for *S. birrea* was by far the highest compared to *H. caffrum*, *P. obliquum* and *R. melanophloeos* (Table 8) It would mean that *S. birrea* results in high inhibition of fungal growth with relative lower toxicity to host cells. Though *H. caffrum*, *P. obliquum* and *R. melanophloeos* resulted in relatively low selectivity indexes, the selectivity index of *R. melanophloeos* was, on average, six times better against *C. albicans* standard strain (ATCC 10231) and clinical isolates than the SI of *P. obliquum*. The selectivity index of *P. obliquum* was, on average, 28 times better against *C. albicans* standard strain (ATCC 10231) and clinical isolates than the SI of *H. caffrum* (Table 8).

TABLE 8

Selectivity index (SI) and LC$_{50}$ values (mg/ml) of acetone leaf extracts of *H. caffrum*,
*P. obliquum* and *R. melanophloeos* and acetone stem bark extract of *S. birrea* against
*C. albicans* standard strain (ATCC 10231) and clinical isolates

| | | *Candida albicans* | | | | | | | |
|---|---|---|---|---|---|---|---|---|---|
| | | ATCC | Clinical isolates | | | | | | |
| Acetone extracts | LC$_{50}$ | 10231 | M0824 | M0825 | M0826 | 1051604 | 1051608 | 1051255 | Average |
| *H. caffrum* (leaf) | 0.002 | 0.001 | 0.001 | 0.001 | 0.004 | 0.004 | 0.004 | 0.001 | 0.002 |
| *P. obliquum* (leaf) | 0.036 | 0.036 | 0.071 | 0.036 | 0.071 | 0.071 | 0.071 | 0.036 | 0.056 |
| *R. melanophloeos* (leaf) | 0.434 | 0.217 | 0.435 | 0.217 | 0.869 | 0.435 | 0.217 | 0.217 | 0.372 |
| *S. birrea* (stem bark) | >1000 | >4.000 | >0.800 | >7.692 | >2.000 | >1.333 | >7.692 | >7.692 | >4.458 |

The data suggests that the antifungal activity of *H. caffrum*, *P. obliquum* and *R. melanophloeos* might be as a result of general metabolic toxins, therefore the low selectivity indices. However, the results of the current study indicate that *P. obliquum* has the highest number of active compounds against *C. albicans* standard strain (ATCC 10231) and clinical isolates. The results also indicate that *H. caffrum* and *R. melanophloeos* had no visible activity against the fungal test organisms as evidenced by the absence of clear zones on TLC bioautograms (Table 6). Minimal inhibitory concentration (MIC) data also indicates that *P. obliquum* is the most active of all the plant species tested against *C. albicans* standard strain (ATCC 10231) and clinical isolates Plants utilize the concept of synergy of different compounds in the extract to combat microbial infections by the interaction of different molecules, which work together to fight off infection. Active compounds have been isolated and developed into chemical drugs for human consumption (Hemaiswarya, et. al., 2008). If a plant exhibits high antimicrobial activity, it may be worth isolating the compounds that contribute to the activity of the plant.

As *P. obliquum* had high activity against the fungal test organisms, with a reasonable selectivity index, the next step involved bioassay-guided fractionation of *P. obliquum* acetone leaf extract.

Example 5

Bioassay Guided Fractionation of Antifungal Compound in *Ptaeroxylon obliquum* (Thunb.) Radlk. Acetone Leaf Extract The active ingredients (chemical compounds) in leaves, roots or bark may be quite different—one part may be very toxic and another part may be harmless. It is therefore very rare that the whole plant will be used for medicinal purposes. Most medicinal plants are used primarily for their leaves and/or twigs, their stem-bark, their underground parts and wood itself is only rarely used (Van Wyk et al., 2009). It is reported that from *P. obliquum* only the wood (Watt and Breyer-Brandwijk, 1962; Hutchings and Van Staden, 1994; Van Wyk et al., 2009) or bark (Hutchings et al., 1996; Van Wyk et al., 2009) itself is used for medicinal purposes. The use of extracts of this plant have previously not been reported against fungi, Reports concerning the isolation of compounds from *P. obliquum* leaves are scant. The wood contains chromones and other phenolic compounds such as ptaeroxylone and umtatin (Dean and Taylor, 1966; Dictionary of Natural Products, 2008; Van Wyk et al., 2009); the leaves contain perforatin A. Perforatin A has antihypertensive effects (Langenhoven et al., 1988; Dictionary of Natural Products, 2008; Van Wyk et al., 2009).

In this example the inventors separated the compounds present into different fractions from the dried acetone leaf extract of *P. obliquum* by means of solvent-solvent fractionation. The active compounds in the solvent-solvent fractions were determined by means of bioautography and TLC-fingerprinting. This antimicrobial activity was determined by measuring the minimal inhibitory concentration (MIC) of the solvent-solvent fractions, obtained from *P. obliquum* acetone leaf extract, after 12 and 24 hours. The cytotoxicity of the solvent-solvent fractions, obtained from *P. obliquum* acetone leaf extract, was also determined using the MTT reduction assay.

Plant Material

Leaves of *P. obliquum* were harvested from a tree growing on the Onderstepoort Campus of the University of Pretoria, South Africa. The leaves were collected in loosely woven orange bags and dried in the dark at room temperature. The dried leaves were ground to powder using a Macsalab mill (Model 200 Lab).

Bulk Extraction

In a bulk extraction, powdered leaves (1000 g) of *P. obliquum* were extracted with acetone at room temperature. The filtrate was collected by passing the mixture through Whatman 185 mm filter paper using a Buchner funnel. The filtrate was concentrated under reduced pressure using a Büchi Rotavapor R-114 at temperatures not exceeding 50° C. The dried extract was weighed before solvent-solvent fractionation was carried out. Approximately 79.52 g of extract was obtained from 1000 g of dried pulverized leaves.

Solvent-Solvent Fractionation

The solvent-solvent extraction/fractionation of plant extracts protocol developed by the National Cancer Institute was modified and used to obtain solvent-solvent fractions from *P. obliquum* acetone leaf extract (Suffness and Douros, 1979; Eloff, 1998c).

Acetone Extraction

The plant material was extracted by dissolving a 10:1 (ml:g) of leaf material in acetone in a container with a closeable lid and placed on the shaking machine for 30 minutes. The solution was left to settle and the clear liquid decanted into a clean, marked new container through filter paper. The process was repeated three times and the filtered solutions combined into one container. The contents was placed in a round bottom flask and evaporated under reduced pressure using a Büchi Rotavapor R-114 rotating at 100 rpm in a water bath at 50° C., The flask was removed from the water just before all the content have evaporated (to prevent heat inactivation or change); kept under vacuum above water level; a small volume of water added to the content and the last traces of acetone removed with the Rotavapor.

Chloroform-Water Fraction

Equal parts of water/chloroform were added to the content in the round bottom flask and after mixing well the contents were poured into a separation funnel. The components separated with the water fraction on the top and the chloroform fraction at the bottom.

Hexane Fraction

The heavier chloroform fraction was evaporated to dryness using a Büchi Rotavapor R-114 under reduced pressure, rotating at 100 rpm in a water bath at 50° C. The flask was removed from the water just before all the contents had evaporated. Equal parts of hexane/chloroform were added to the contents in the round bottom flask and after mixing well the contents were poured into a separation funnel. The components separated with the hexane fraction on the top and the chloroform fraction at the bottom.

Ethyl Acetate Fraction

The heavier chloroform fraction was evaporated to dryness using a Büchi Rotavator R-114 under reduced pressure, rotating at 100 rpm in a water bath at 50° C. The flask was removed from the water just before all the contents had evaporated. Equal parts of ethyl acetate and chloroform were added to the contents in the round bottom flask and after mixing well the content were poured into a separation funnel. The components separated with the ethyl acetate fraction on the top and the chloroform fraction at the bottom.

Thin Layer Chromatography (TLC)

After solvent-solvent fractionation, solutions of 10 mg/ml of each fraction were prepared in acetone. A sonicator was used to enhance the solubility of each fraction. For each fraction, 10 μl aliquots (100 μg) were loaded on aluminium-backed TLC plates (Merck Silica $F_{254}$ plates) and developed in various mobile phases of varying polarities. Hexane:ethyl acetate [70:30]; hexane:ethyl acetate [50:50] and chloroform:methanol [95:5] were used as solvent systems. Duplicate TLC plates were visualised under ultraviolet (UV) light and visible spots were circled. For visualization of non-fluorescing spots, plates were sprayed with vanillin spray reagent (0.1 g vanillin dissolved in 28 ml methanol and 1 ml sulphuric acid added) and heated at 100° C. for 5 min. Plates were scanned, using a HP Scanjet 5470c scanner, immediately after heating to record the chromatograms.

Bioautography Procedure

The chromatograms were dried for 5 days at room temperature to remove the eluent solvent systems. Developed TLC plates were sprayed with a concentrated suspension of the fungal test organism (*C. albicans* standard strain (ATCC 10231) and clinical isolates) prepared in Sabouraud dextrose broth in a Biosafety Class II cabinet (Labotec, SA). The sprayed plates were placed in a humid chamber (100 percent relative humidity) and incubated overnight at 25° C. Plates were then sprayed with a 2 mg/ml p-iodonitro-tetrazolium violet (INT, Sigma) solution and incubated at 25° C. until a purple-red colour change was evident. Plates with white bands where reduction of INT to formazan did not occur were tightly sealed in transparent plastic bags and retardation factor ($R_f$) values of inhibitory zones recorded.

The bioautography procedure was repeated on two separate occasions.

Figure 6:
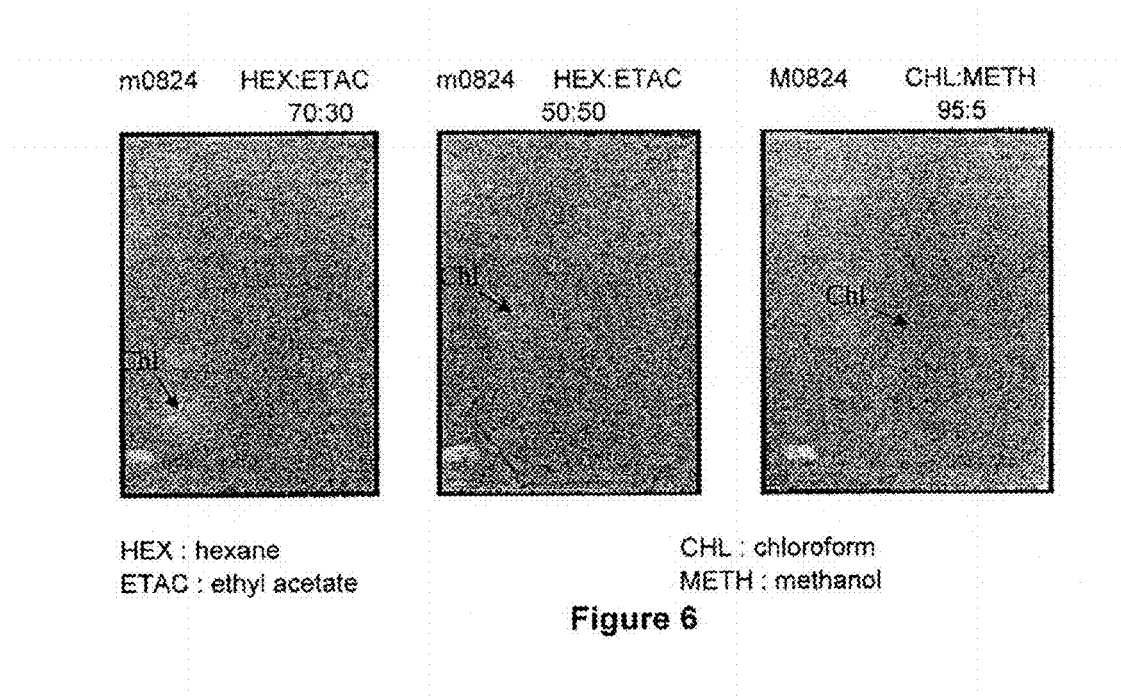
FIG. 6: TLC Bioautograms

The compounds whose retardation factor ($R_f$) values are listed in Table 9 were identified as the active constituents that displayed growth inhibition of the *C. albicans* standard strain (ATCC 10231) and clinical isolates tested. The chloroform-fraction had the highest number of compounds against the opportunistic pathogen *C. albicans* and clinical isolates (FIG. 6).

TABLE 9

The $R_f$ values of active compounds from the solvent-solvent fractions obtained from *P. obliquum* acetone leaf extract against *C. albicans* standard strain (ATCC 10231) and clinical isolates

| Fraction | Eluting solvent system | *Candida albicans* | | | | | |
| --- | --- | --- | --- | --- | --- | --- | --- |
| | | ATCC | Clinical isolates | | | | |
| | | 10231 | M0824 | M0825 | 1051604 | 1051608 | 1051255 |
| Chloroform | HEX:ETAC 50:50 | 0.65 | 0.7 | 0.72 | 0.91 | 0.69 | 0.75 |
| | | 0.49 | 0.43 | 0.56 | 0.76 | 0.49 | 0.41 |
| | | 0.38 | 0.04 | 0.44 | 0.43 | 0.4 | — |
| | HEX:ETAC 70:30 | 0.44 | 0.38 | 0.38 | — | 0.38 | — |
| | | — | 0.13 | 0.15 | — | 0.15 | — |
| | CHL:METH 95:05 | 0.89 | 0.9 | 0.92 | — | — | — |
| | | 0.57 | 0.57 | 0.57 | — | 0.59 | 0.54 |
| | | 0.43 | 0.43 | 0.43 | 0.49 | 0.44 | 0.43 |
| | | 0.22 | 0.19 | 0.25 | — | — | — |
| Hexane | HEX:ETAC 50:50 | 0 | 0.84 0 | 0.03 | 0 | 0 | 0.02 |
| | HEX:ETAC 70:30 | 0 | 0 | 0 | 0 | 0 | 0.01 |
| | CHL:METH 95:05 | 0 | 0.93 0 | 0.92 0.03 | 0 | 0 | 0 |
| ETAC$_1$ | HEX:ETAC 50:50 | 0.19 | — | 0.2 | 0.19 | — | 0.18 |
| | HEX:ETAC 70:30 | — | — | — | — | — | — |
| | CHL:METH 95:05 | — | — | — | — | — | — |

TABLE 9-continued

The $R_f$ values of active compounds from the solvent-solvent fractions obtained from *P. obliquum* acetone leaf extract against *C. albicans* standard strain (ATCC 10231) and clinical isolates

| Fraction | Eluting solvent system | Candida albicans ATCC 10231 | Clinical isolates M0824 | M0825 | 1051604 | 1051608 | 1051255 |
|---|---|---|---|---|---|---|---|
| ETAC$_2$ | HEX:ETAC 50:50 | — | — | — | — | — | — |
| | HEX:ETAC 70:30 | — | — | — | — | — | — |
| | CHL:METH 95:05 | — | — | — | — | — | — |
| ETAC$_{21}$ | HEX:ETAC 50:50 | — | — | — | — | — | — |
| | HEX:ETAC 70:30 | — | — | — | — | — | — |
| | CHL:METH 95:05 | — | — | — | — | — | — |
| H$_2$0 | HEX:ETAC 50:50 | — | — | — | — | — | — |
| | HEX:ETAC 70:30 | — | — | — | — | — | — |
| | CHL:METH 95:05 | — | — | — | — | — | — |

$R_f$: retardation factor
HEX: hexane
ETAC: ethyl acetate
ETAC$_1$: ethyl acetate (Sep. 2, 2010)
ETAC$_2$: ethyl acetate (Oct. 2, 2010)
ETAC$_{21}$: ethyl acetate (Oct. 2, 2010)
CHL: chloroform
METH: methanol
H$_2$O: water
—: no visible activity The water and ethyl acetate (ETAC$_2$ and ETAC$_{21}$) fractions had no visible activity against the test organisms as evidenced by the absence of clear zones on TLC bioautograms. The hexane fraction was active against all the strains tested. However, for the hexane fraction a $R_f$ value of mostly zero was recorded. This suggests that the chemical constituent in the hexane fraction is highly polar in nature.

Fungal Cultures

*Candida albicans* standard strain (ATCC 10231) and clinical isolates (obtained from the Department of Microbiology, National Health Laboratory Services, Pretoria, South Africa) were maintained on Sabouraud dextrose agar at 4° C. to prevent overgrowing and morphological changes. Subcultures were freshly prepared before use. Inocula were prepared from the 24 h cultures by transferring colonies from the freshly prepared subcultures to Sabouraud dextrose broth.

Minimal Inhibitory Concentration (MIC) Determination

To determine the MIC values, the microplate dilution method developed by Eloff (1998b) with modifications for antifungal activity assay by Masoko et al. (2005) was used.

The assay was initiated by pouring sterile water aliquots (100 µl) into the wells of a 96-well microtitre plate. Exactly 100 µl of a 10 mg/ml fraction (chloroform, hexane, water, ethyl acetate) was added in row A and mixed using a micropipette. From row A 100 µl was aspirated and added into row B and mixed. The procedure was repeated until all the wells were filled. An additional 100 µl in row H was discarded. 100 µl of *C. albicans* standard strain (ATCC 10231) or clinical isolates (transferred to Sabouraud dextrose broth until a turbidity of MacFarlane Standard 1=4× $10^7$ CFU was reached) was added to the wells of the microtitre plate. 50 µl of a 0.2 mg/ml aqueous solution of p-iodonitro-tetrazolium violet (INT, Sigma) was added to each well. The plates were incubated at 35° C. for 12 h and 24 h. Inhibition of microbial growth was indicated by the failure of the well to change colour; uninhibited growth was a pink colour. Amphotericin B was used as a positive control; acetone was used as a negative control. The experiment was performed in triplicate and on two separate occasions.

All the fractions showed anti-candidal activity against the *C. albicans* standard strain and clinical isolates tested (Table 10). Inhibition at concentrations <1 mg/ml, against the *C. albicans* standard strain (ATCC 10231) tested, was observed after 12 h for the hexane (0.63 mg/ml), chloroform (0.63 mg/ml), ETAC$_1$ (0.63 mg/ml) and ETAC$_2$ (0.63 mg/ml) fractions. The antifungal compound, Amphotericin B, inhibited the growth of *C. albicans* standard strain (ATCC 10231) and clinical isolates (Table 10).

Even at the highest concentrations tested (2.50 mg/ml), the water fraction did not inhibit the growth of *C. albicans* standard strain (ATCC 10231) and clinical isolates (Table 10). These results support the results of Kotze and Eloff (2002) that water extracts generally do not have antimicrobial activity. Acetone, the negative control, did not inhibit the growth of any of the strains tested.

TABLE 10

Minimal inhibitory concentrations for the solvent-solvent fractions and amphotericin B

|  |  | *MIC (mg/ml) Candida albicans | | | | | | |
|---|---|---|---|---|---|---|---|---|
| Fractions/ | Time of | ATCC | Clinical isolates | | | | | |
| Amphotericin B | incubation (h) | 10231 | M0824 | M0825 | M0826 | 1051604 | 1051608 | 1051255 |
| Hexane | 12 | 0.63 | 0.16 | 0.08 | 0.63 | 0.31 | 0.63 | 0.63 |
|  | 24 | 1.25 | 1.25 | 0.31 | 0.63 | 1.25 | 1.25 | 1.25 |
| Chloroform | 12 | 0.63 | 0.16 | 0.08 | 0.31 | 0.31 | 0.63 | 0.31 |
|  | 24 | 1.25 | 0.16 | 0.16 | 0.63 | 1.25 | 1.25 | 1.25 |
| $ETAC_1$ | 12 | 0.63 | 0.16 | 0.16 | 1.25 | 1.25 | 2.5 | 0.31 |
|  | 24 | 2.5 | 0.31 | 0.31 | 2.5 | >2.50 | >2.50 | >2.50 |
| $H_2O$ | 12 | >2.50 | 0.31 | 0.63 | >2.50 | >2.50 | >2.50 | >2.50 |
|  | 24 | >2.50 | >2.50 | 2.5 | >2.50 | >2.50 | >2.50 | >2.50 |
| $ETAC_2$ | 12 | 0.63 | 0.31 | 0.16 | 1.25 | 1.25 | 2.5 | 1.25 |
|  | 24 | 2.5 | 0.31 | 0.31 | 1.25 | 1.25 | >2.50 | 2.5 |
| $ETAC_{21}$ | 12 | 1.25 | 0.31 | 0.16 | 1.25 | 1.25 | 1.25 | 1.25 |
|  | 24 | 2.5 | 0.31 | 1.25 | 1.25 | 2.5 | 2.5 | 2.5 |
| Amphotericin B | 12 | 0.11 | 0.03 | 0.03 | 0.06 | 0.06 | 0.11 | 0.03 |
|  | 24 | 0.11 | 0.11 | 0.06 | 0.11 | 0.06 | 0.11 | 0.23 |

*MIC: Minimal inhibitory concentration representing the mean value
$H_2O$: water
$ETAC_2$: ethyl acetate (Oct. 2, 2010)
h: hours
$ETAC_1$: ethyl acetate (Sep. 2, 2010)
$ETAC_{21}$: ethyl acetate (Oct. 2, 2010)

To investigate the extreme variation in MIC values of some fractions with time of incubation (12 h and 24 h); wells were re-inoculated onto Sabouraud dextrose agar plates and re-incubated at 35° C. for 24 h (Table 11). Thus, the cidal/static effects of the fractions and/or Amphotericin B on C. albicans standard strain (ATCC 10231) and clinical isolates could be determined.

TABLE 11

Effect of the fractions/amphotericin B, re-inoculated and re-incubated, on the C. albicans strains tested

| C. albicans strain | Fraction/ Amphotericin B | *MIC | | Growth after re-inoculation and re-incubation | Cidal/ static effects |
|---|---|---|---|---|---|
|  |  | 12 h | 24 h |  |  |
| ATCC 10231 | $ETAC_1$ | 0.63 | 2.50 | no | cidal |
|  | $ETAC_2$ | 0.63 | 2.50 | yes | static |
| M0824 | Hexane | 0.16 | 1.25 | yes | static |
|  | $H_2O$ | 0.31 | >2.50 | yes | static |
|  | Amphotericin B | 0.03 | 0.11 | yes | static |
| M0825 | Hexane | 0.08 | 0.31 | no | cidal |
|  | $H_2O$ | 0.63 | >2.50 | yes | static |
|  | $ETAC_{21}$ | 0.16 | 1.25 | no | cidal |
| 1051604 | Hexane | 0.31 | 1.25 | yes | static |
|  | Chloroform | 0.31 | 1.25 | yes | static |
|  | $ETAC_1$ | 1.25 | >2.50 | yes | static |
| 1051255 | Chloroform | 0.31 | 1.25 | yes | static |
|  | $ETAC_1$ | 0.31 | >2.50 | yes | static |
|  | Amphotericin B | 0.03 | 0.23 | yes | static |

*MIC: Minimal inhibitory concentration representing the mean value
$ETAC_1$: ethyl acetate (Sep. 2, 2010)
$ETAC_2$: ethyl acetate (Oct. 2, 2010)
h: hours
$H_2O$: water
$ETAC_{21}$: ethyl acetate (Oct. 2, 2010)

Cytotoxicity of the Solvent-Solvent Fractions

The MTT [3-(4.5-dimethylthiazolyl)2.5-diphenyltetrazolium bromide] reduction assay of Mosmann (1983) was used for measuring cell proliferation and cytotoxicity (described in greater detail above). MTT (yellow) is reduced into a formazan (purple) by viable cells. The colour intensity of the formazan produced, which is directly proportional to the number of viable cells, is measured using a spectrophotometer (Mosmann, 1983).

Figure 13:
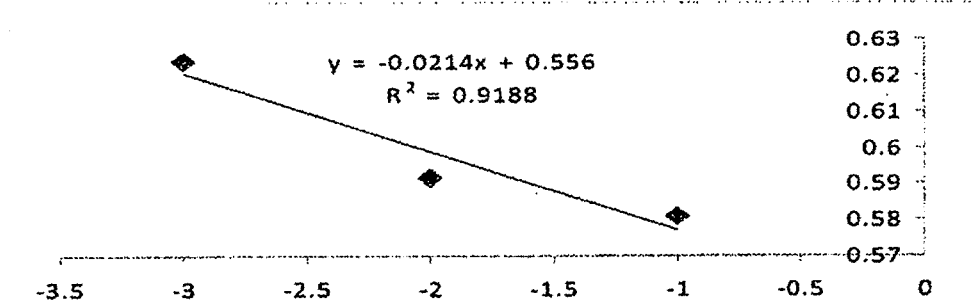
FIG. 13: Cytotoxicity of berberine ($LC_{60}$=9.04 μg/ml) against mouse fibroblast cells

The cytotoxicity of the solvent-solvent fractions, obtained from P. obliquum acetone leaf extract, was determined against mouse fibroblast cells using the MTT assay. The results are presented in FIGS. 11, 12, 13, 14, 15 and 16 and in Table 12. Berberine was used as a positive control and was found to be toxic with a $LC_{50}$ of 9.04 µg/ml (FIG. 13)

The selectivity indices for the solvent-solvent fractions were calculated by dividing the $LC_{50}$ in mg/ml by the MIC in mg/ml.

The selectivity index is the ratio of the efficacy against the pathogen relative to the toxicity to the cells. It relates to the degree to which the observed activity of a substance can be attributed to the toxicity of that substance. A high value indicates good efficacy and low toxicity. A value lower than one indicates that the treatment is more harmful to cells than to the pathogen. The selectivity indices were substantially lower than one with all fractions (Table 12).

The selectivity index (Table 12) was the highest for the $EATC_1$-fraction. The selectivity index of the hexane- and $ETAC_1$-fraction was, on average, four times better against C. albicans standard strain (ATCC 10231) and clinical isolates than that resulting from the chloroform-fraction (Table 12).

The data (Table 12) suggests that the antifungal activity of the solvent-solvent fractions, obtained from P. obliquum acetone leaf extract, may be related to a general metabolic toxin leading to the low selectivity indices.

TABLE 12

Selectivity index (SI) and LC50 values (mg/ml) of the solvent-solvent fractions, obtained from *P. obliquum* acetone leaf extract, against *C. albicans* standard strain (ATCC 10231) and clinical isolates

| | | *Candida albicans* | | | | | | | |
|---|---|---|---|---|---|---|---|---|---|
| | | ATCC | Clinical isolates | | | | | | |
| Fractions | $LC_{50}$ | 10231 | M0824 | M0825 | M0826 | 1051604 | 1051608 | 1051255 | Average |
| Hexane | 0.212 | 0.169 | 0.169 | 0.683 | 0.336 | 0.169 | 0.169 | 0.169 | 0.266 |
| Chloroform | 0.029 | 0.022 | 0.179 | 0.179 | 0.045 | 0.022 | 0.022 | 0.022 | 0.07 |
| $ETAC_1$ | 0.229 | 0.091 | 0.740 | 0.740 | 0.091 | >0.091 | >0.091 | >0.091 | 0.276 |
| $ETAC_2$ | 0.039 | 0.015 | 0.128 | 0.128 | 0.031 | 0.031 | >0.015 | 0.015 | 0.015 |
| $ETAC_{21}$ | 0.071 | 0.028 | 0.229 | 0.057 | 0.057 | 0.028 | 0.028 | 0.028 | 0.065 |

$ETAC_1$: ethyl acetate (Sep. 2, 2010)
$ETAC_2$: ethyl acetate (Oct. 2, 2010)
$ETAC_{21}$: ethyl acetate (Oct. 2, 2010)

The results of the current example indicate that the chloroform-fraction has the highest number of active compounds against *C. albicans* standard strain (ATCC 10231) and clinical isolates (FIG. 6, Table 9). Minimal inhibitory concentration (MIC) data also indicate that the chloroform-fraction is the most active of all the solvent-solvent fractions against *C. albicans* standard strain (ATCC 10231) and clinical isolates tested (Table 10).

The low selectivity indices of the fractions indicate that there is hardly any chance that these could be used for therapeutic purposes. It has to be taken into account that cellular toxicity does not necessarily equate to whole animal toxicity because factors such as changes in the gut, bioavailability issues may lead to large differences. If extracts are to be used as a gargle against *Candida* with short term exposure it may still be possible to use it.

It is not necessarily the compounds responsible for the anticandidal effect that are toxic to the cells. It may therefore be worth isolating the compounds that contribute to the activity. If some of these compounds are active against *Candida* and not toxic to human cells it may lead to an oral hygiene product that can protect patients against oral *Candida* infections.

Following this finding, the next step therefore involves the bioassay-guided isolation of the antifungal compounds from the chloroform-fraction, obtained from *P. obliquum* acetone leaf extract.

Example 6

Bioassay-Guided Isolation of the Antifungal Compounds from the Chloroform-Fraction Obtained from *P. obliquum* (Thunb.) Radlk. Acetone Leaf Extract Ptaeroxylaceae is a small family comprising two genera, *Ptaeroxylon*, and *Cedrelopsis*. *Ptaeroxylon*, is a monotypic genus comprising only the southern African species, *Ptaeroxylon obliquum*; whereas *Cedrelopsis* is a genus limited to Madagascar and contains several species (Mulholland et al., 2000). *Ptaeroxylon* and *Cedrelopsis* are grouped and placed in the Ptaeroxylaceae family, based on the structure of the secondary xylem and their similar pollen morphology (Styles and Pennington, 1975). *P. obliquum* contains a wide variety of simple and prenylated 6,7-dioxygenated coumarins and 5,7-dioxygenated prenylated chromones (Dean and Taylor, 1966; Mulholland et al., 2000). An ethyl acetate extract of ground *P. obliquum* heartwood contains the chromones peucenin, found previously in the roots of *Peucedanum ostruthium* Koch (Umbelliferae); desoxykarenin and karenin; as well as isomeric coumarins 7-0-(3,3-dimethylallyl) scopoletin, nieshoutin and nieshoutol; and the ubiquitous β-sistosterol (McCabe at al., 1967). A re-investigation of the bark of *P. obliquum* yielded the unusual aromadendrane diterpenoid, cneorubin X (Mulholland et al., 2000). The isolated limonoids cedmiline and cedmilinol most closely resemble those reported previously from the Cneoraceae, for example, cneorin K from *Neochamaela pulverulenta* (Mondon at al., 1978). The Cneoraceae also produced prenylated coumarins and cneorubin X has previously been isolated rom *Cneorum tricoccon* (Trautmann et al., 1980). Thus, chemical analysis indicates that the Ptaeroxylaceae may be closely related to the Cneoraceae family.

However, little is known in the literature concerning the isolation of compounds from *P. obliquum* leaves. The leaves are reported to contain Perforatin A which has antihypertensive effects (Langenhoven et al., 1988; Dictionary of Natural Products, 2008; Van Wyk at al., 2009).

In this example the inventors isolated active antifungal compounds (against *C. albicans* standard strain (ATCC 10231) and clinical isolates), obtained from *P. obliquum* acetone leaf extract, identified as the most active solvent-solvent fraction after bioautography and minimal inhibitory concentration (MIC) determination.

Selection of Stationary Phase

Column chromatography using silica gel (Merck, Silica Gel G60) as the stationary phase was chosen for separation of compounds for the following reasons: (1) separation on silica gel represents one of the cheapest methods for isolation of compounds; (2) silica gel is readily accessible and preparation of separating systems is simple and quick; and (3) eluent system polarity can be varied to adjust elution of active compounds.

Group Separation (Column I)

Silica gel (800 g) was mixed with hexane to form a homogenous suspension/slurry and stirred using a stirring rod to remove bubbles. The silica gel slurry was poured into a glass column (10 cm diameter and 50 cm length) whose outlet was plugged with cotton wool to retain the gel in the column. The solvent was allowed to flow out of the column opening to allow the gel to settle.

The chloroform-fraction (extract) sample was prepared by dissolving 15 g of the extract in 100 ml of ethyl acetate. To the solution, 30 g of silica was added, and mixed by stirring with a glass rod. The mixture was allowed to dry at room temperature under a stream of air for approximately 5 hours. The dried silica gel-extract mixture was carefully layered on the column gel bed. For elution hexane was used as the first mobile phase with the polarity increasing by 10% increments of ethyl acetate. For each eluent mixture 1.5 L volumes were used and 500 ml fractions collected in glass beakers. The 22 collected fractions were concentrated using a Büchi R-114 Rotavapor. TLC was used to analyse fractions, and those with similar chemical components were combined.

Combination of Fractions from Column I (Chloroform Extract/Fraction)

The antimicrobial activities of the fractions were assayed using bioautography as the method of choice with *C. albicans* standard strain (ATCC 10231) and clinical isolates as fungal test organisms. In most instances active compounds were found in more than one fraction. These fractions were combined to maximise the level of active compounds in order to obtain a high yield of the compounds.

Isolation of Compound C1 (Column II)

A glass column with length of 50 cm and diameter of 2 cm was used for fractionation. Silica gel (150 g) was mixed with hexane by stirring and the slurry poured into the column whose bottom opening was plugged with cotton wool. The solvent was allowed to drip out of the silica gel to settle and establish a column bed. The sample was prepared by mixing 2 g of the fraction with 4 g silica gel in 60 ml of ethyl acetate. The mixture was stirred vigorously and dried under a stream of air. The dried sample was loaded onto the gel in the column. After a series of separations of the fraction on TLC plates in different solvent mixtures to obtain a system resulting in good resolution, hexane:ethyl acetate [70:30] was selected as the solvent system. The loaded column was eluted using hexane:ethyl acetate [70:30] mixture with 50 ml fraction volumes collected at 5 ml/min.

Isolation of Compound C2 (Column III)

Fractions containing similar antifungal compounds were combined and the mixture used for isolation of compound C2. A glass column with a length of 40 cm and diameter of 4 cm was used for fractionation of the mixture. Silica gel (200 g) was mixed with hexane by stirring and the slurry poured into the column whose bottom opening was plugged with cotton wool. The solvent was allowed to drip out to settle the gel and establish a column bed. The sample was prepared by mixing 3 g of the fraction mixture with 6 g silica gel in 90 ml ethyl acetate. The mixture was stirred vigorously and dried under a stream of air. The dried sample was then loaded onto the gel bed and eluted with hexane:ethyl acetate [50:50] mixture with polarity increased by 10% increments of ethyl acetate. Fifty ml fractions were collected at a flow rate of 5 ml/min.

Results and Discussion

Figure 14:
FIG. 14: TLC bioautograms showing activity of fractions against *C. albicans* isolates
Figure 14:
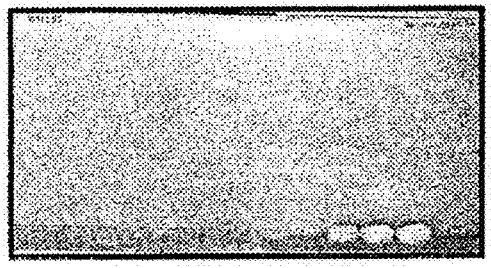
Figure 14:
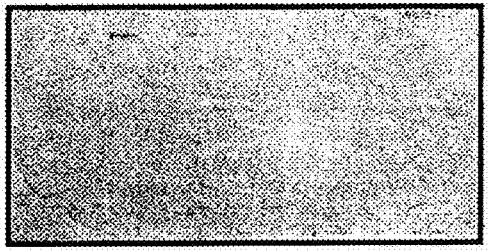
Figure 15:
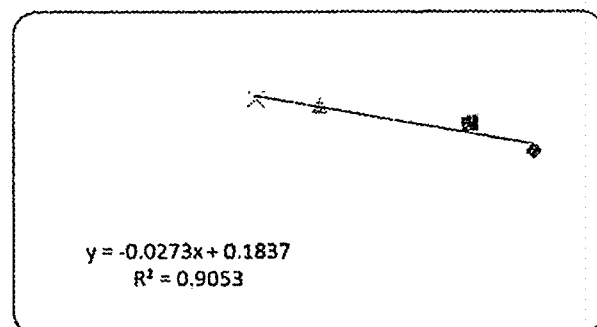
FIG. 15: Cytotoxicity of Compound 1 (0.001 μg/ml) against mouse fibroblast cells
Figure 16:
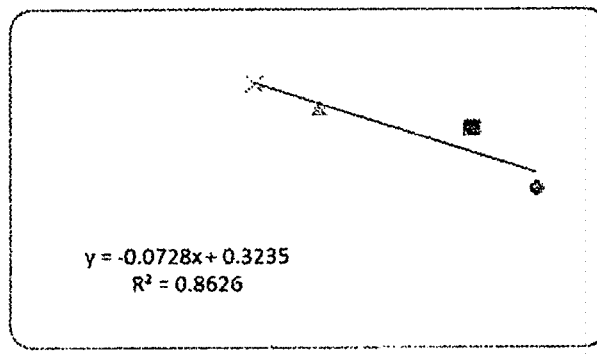
FIG. 16: Cytotoxicity of Compound 2 (7.23 μg/ml) against mouse fibroblast cells

From column I, 22 fractions were collected and analysed on TLC plates. The fractions containing compounds with $R_f$ corresponding to the $R_f$ values of bioautography assay were combined (Table 13). These fractions were tested for antifungal activity (FIG. 14). Active fractions were identified for isolation of anti-candidal compounds. The purification of the compounds was achieved by repeated column chromatography until a single spot was obtained from each compound using three different mobile phases to develop the chromatograms.

TABLE 13

The $R_f$ values of active fractions against *C. albicans* and two clinical isolates

| Eluting Solvent System | Fractions | *C. albicans* isolates | |
|---|---|---|---|
| | | 1051604 | 1051255 |
| HEX:ETAC 70:30 | 3 | — | 0.89 |
| | 5 | — | 0.89 |
| | 7 | — | 0.3 |
| | 8 | — | 0.31 |
| | 9 | — | 1 |
| | 10 | — | 1 |

TABLE 13-continued

The $R_f$ values of active fractions against *C. albicans* and two clinical isolates

| Eluting Solvent System | Fractions | *C. albicans* isolates | |
|---|---|---|---|
| | | 1051604 | 1051255 |
| HEX:ETAC 50:50 | 19 | 0.3 | 0.45 |
| | 20 | 0.3 | 0.45 |

Rf: retardation factor
HEX: hexane
ETAC: ethyl acetate
—: no visible activity

Two active antifungal compounds were isolated using silica gel as the stationary phase in column chromatography, following the principles of bioassay-guided fractionation. This is the first report of isolation and identification of compounds with antifungal activity from *P. obliquum* leaves.

Example 7

Biological Activity of the Isolated Compounds and Structure Elucidation

Two compounds were isolated from the most active fraction obtained from *Ptaeroxylon obliquum* acetone leaf extract, using column chromatography with silica gel as the stationary phase. In the available literature, very little information about compounds isolated from *P. obliquum* leaves was found. The leaves contain perforatin A which has antihypertensive effects (Langenhoven et al., 1988; Dictionary of Natural Products, 2008; Van Wyk et al., 2009).

In this example the inventors determined the antifungal activity and cytotoxicity of the isolated compounds and elucidated the structures of the two isolated compounds, obtained from *P. obliquum* acetone leaf extract.

Fungal Cultures

*Candida albicans* standard strain (ATCC 10231) and clinical isolates (obtained from the Department of Microbiology, National Health Laboratory Services, Pretoria, South Africa) were maintained on Sabouraud dextrose agar at 4° C. to prevent overgrowing and morphological changes.

Subcultures were freshly prepared on Sabouraud dextrose agar before use. Inocula were prepared from the 24 h cultures.

Minimal Inhibitory Concentration (MIC) Determination

To determine the MIC values, the microplate dilution method developed by Eloff (1998b) with modifications for antifungal activity assay by Masoko et al. (2005) was used.

The assay was initiated by pouring sterile water aliquots (100 μl) into the wells of a 96-well microtitre plate. Exactly 100 μl of the 1 mg/ml compound was added in row A and mixed using a micropipette. From row A 100 μl was aspirated and added into row B and mixed. The procedure was repeated until all the wells were filled. An additional 100 μl in row H was discarded. 100 μl of *C. albicans* standard strain (ATCC 10231) or clinical isolates (transferred to Sabouraud dextrose broth until a turbidity of MacFarlane Standard $1=4\times10^7$ CFU was reached) were added to the wells of the microtitre plate. 50 μl of a 0.2 mg/ml aqueous solution of p-iodonitro-tetrazolium violet (INT, Sigma) was added to each well. The plates were incubated at 35° C. for 12 h and 24 h. Inhibition of microbial growth was indicated by the failure of the well to change colour; uninhibited growth was a pink colour. Amphotericin B was used as a positive control; acetone was used as a negative control. The experiment was performed in triplicate and on two separate occasions.

Both compounds had anti-candidal activity against the *C. albicans* standard strain (ATCC 10231) and clinical isolates tested (Table 14). Amphotericin B inhibited the growth of *C. albicans* standard strain (ATCC 10231) and clinical isolates (Table 14).

TABLE 14

Minimal inhibitory concentrations for the Compounds and amphotericin B tested

| Compounds/ Amphotericin B | Incubation time (h) | *MIC (mg/ml) Candida albicans | | | | | | |
|---|---|---|---|---|---|---|---|---|
| | | ATCC 10231 | Clinical isolates | | | | | |
| | | | M0824 | M0825 | M0826 | 1051604 | 1051608 | 1051255 |
| Compound 1 | 12 | 0.004 | >0.25 | >0.25 | >0.25 | >0.25 | 0.004 | >0.25 |
| | 24 | 0.004 | >0.25 | >0.25 | >0.25 | >0.25 | 0.25 | >0.25 |
| Compound 2 | 12 | 0.004 | >0.25 | >0.25 | >0.25 | >0.25 | 0.008 | >0.25 |
| | 24 | 0.004 | >0.25 | >0.25 | >0.25 | >0.25 | 0.25 | >0.25 |
| Amphotericin B | 12 | 0.11 | 0.03 | 0.03 | 0.06 | 0.06 | 0.11 | 0.03 |
| | 24 | 0.11 | 0.11 | 0.06 | 0.11 | 0.06 | 0.11 | 0.23 |

*MIC: Minimal inhibitory concentration representing the mean value
H: hours

Compound 1 and Compound 2 inhibited the growth of *C. albicans* standard strain (ATCC 10231) at a much lower value (0.004 mg/ml) as compared to amphotericin B (0.11 mg/ml) (Table 14).

There appeared a remarkable interaction in the activity of compound 2 and amphotericin B with the different isolates. In the ATCC strain compound 2 was much more active but in the clinical isolates it was generally much less active.

Cytotoxicity

The MTT [3-(4.5-dimethylthiazolyl)2.5-diphenyltetrazolium bromide] reduction assay of Mosmann (1983) was used for measuring cell proliferation and cytotoxicity. MTT (yellow) is reduced into a formazan (purple) by viable cells. The colour intensity of the formazan produced, which is directly proportional to the number of viable cells, is measured using a spectrophotometer (Mosmann, 1983).

Figure 17:
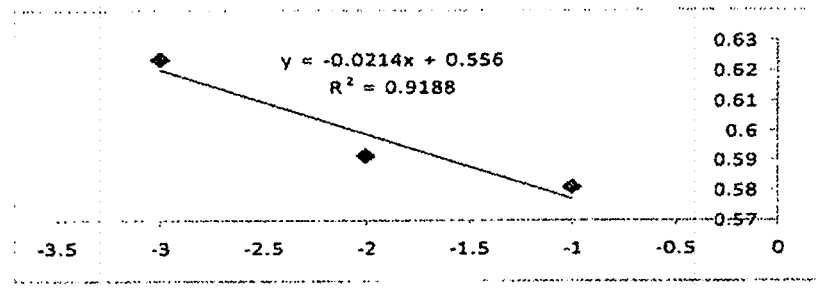
FIG. 17: Cytotoxicity of berberine ($LC_{50}$=9.04 μg/ml) against mouse fibroblast cells

The cytotoxicity of the compounds was determined against mouse fibroblast cells using the MTT assay. The results are presented in FIGS. 19 and 20. Berberine was used as a positive control and was found to be toxic with a $LC_{50}$ of 9.04 μg/ml (FIG. 17).

Selective activity of the compounds was calculated as follows:

Selectivity index (SI)=$LC_{50}$ against mouse fibroblast cells/MIC in same units The selectivity index is calculated to determine the relationship of activity of a test product to its cytotoxic concentration. The higher the number the safer the product. The selectivity index obtained for Compound 2 was by far the highest compared to Compound 1 (Table 15). This would mean that Compound 2 results in high inhibition of fungal growth with relative lower toxicity to host cells. Unfortunately only in the case of the clinical *C. albicans* isolate was the value higher than one and would the product be safe to use Structure Elucidation The structures of the compounds were determined by extensive nuclear magnetic resonance (NMR) techniques and chemical methods mainly by 1D NMR ($^1$H, $^{13}$C and DEPT) and 2D NMR (HSQC, HMBC and COSY) and by comparison with the literature data. About 1 mg of each compound was submitted for spectrometric analysis at the Department of Chemistry, University of Pretoria. Electron impact mass spectrometry (EMS) was used to analize the isolated compounds.

Compound 1

Compound 1 was obtained as isomeric mixture; the TLC fingerprint indicated unresolved single spot with three different mobile phases. However, the 1D and 2D NMR spectra exhibited chemical shift characteristic of both olean-12-ene and lupene. 13C NMR (DMSO): 145.20 (C-13, olean), 121.72 (C-12, olean); 150.97 (C-20, lup); 109.31 (C-29, lup); 41 (C-18, olean), 48.30 (C-18, lup), 27.97 (C-19, olean), 48.00 (C-19, lup) (Table 16).

Figure 18:
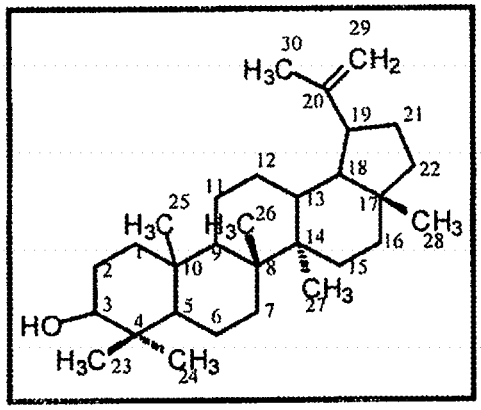
FIG. 18: The structure of Compound 1.1 (Lupeol) isolated from *P. obliquum* leaves

From the HMBC, methyl group (C-29) resonance at δH 1.62 (δC 19.28) showed correlation to a methine at δC 48.29 (C-19), methylene carbon resonance at 109.31 and unsaturated carbon resonance at δC 150.97 (C-20). These correlations are characteristic feature of lupeol (FIG. 18).

TABLE 15

Selectivity index (SI) of the isolated Compounds against *C. albicans* standard strain (ATCC 10231) and clinical isolates

| | Candida albicans | | | | | | | |
|---|---|---|---|---|---|---|---|---|
| | ATCC | Clinical isolates | | | | | | |
| Compounds | 10231 | M0824 | M0825 | M0826 | 1051604 | 1051608 | 1051255 | Average |
| Compound 1 | 0.0003 | <0.000 | <0.000 | <0.000 | <0.000 | 0 | <0.000 | 0 |
| Compound 2 | 1.808 | <0.029 | <0.029 | <0.029 | <0.029 | 0.029 | <0.029 | 0.283 |

Figure 18: The structure of Compound 1.1 (lupeol) isolated from P. obliquum leaves

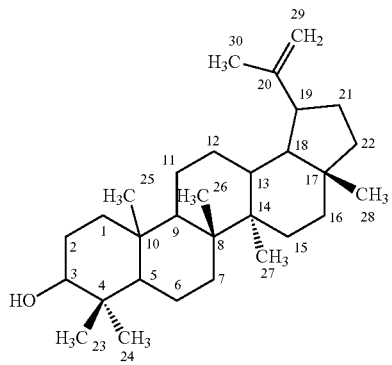

Methyl group (C-27) resonance at δH 1.05 (δC 26.93) showed correlation to a methylene at δC 27 (C-15), two quaternary carbon resonance at 39.79 (C-8) and 41.71 (C-14), and unsaturated carbon resonance at δC 145.20 (C-13). These correlations are characteristic feature of β-amyrin (FIG. 19).

Figure 19:
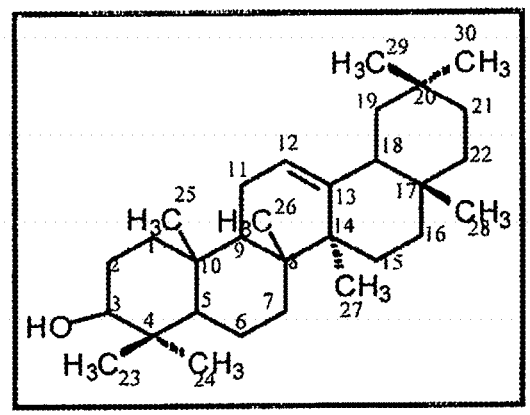
FIG. 19: The structure of Compound 1.2 (β-amyrin) isolated from *P. obliquum* leaves

Figure 19: The structure of Compound 1.2 (β–amyrin) isolated from P. obliquum leaves

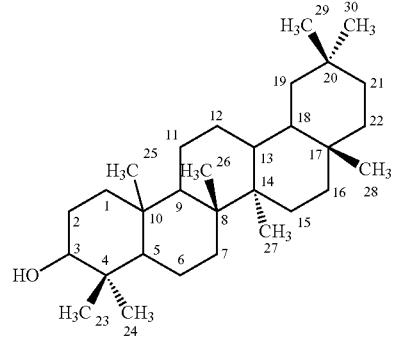

The methyl group (C-23) resonance at δH 0.98 (δC 27.00) showed correlation to a methyl group resonance at δC 18.36 (C-24), methine carbon resonance at 55.16 (C-5) and 79.00 (C-3). The methyl group (C-24) resonance at δH 0.79 (δC 18.38) showed correlation to a methylene at δC 27.00 (C-23), methine carbon resonance at 55.16 (C-5) and 79.00 (C-3). These correlations are characteristic feature of both β-amyrin and lupeol. Comparing the data with the literature values (Table 16), the two compounds in the mixture were identified to be β-amyrin and lupeol (Mahato and Kundu, 1994).

TABLE 16

$^{13}$C NMR data of Compound 1.1 (lupeol) and Compound 1.2 (β-amyrin) compared with literature data (Mahato and Kudu, 1994)

| Carbon position | β-amyrin (red colour represent the lupeol) | | |
|---|---|---|---|
| | DEPT | C-13 | Literature |
| 1 | CH$_2$ | 38.81 | 38.7 |
| 2 | CH$_2$ | 27.46 | 27.2 |
| 3 | CH | 79.02 | 79.0 |
| 4 | C | 40.01 | 38.6 |
| 5 | CH | 55.40 | 55.3 |
| 6 | CH$_2$ | 18.61 | 18.5 |
| 7 | CH$_2$ | 32.88 | 32.8 |
| 8 | CH | 38.81 | 38.80 |
| 9 | CH | 47.85 | 47.7 |
| 10 | C | 37.35 | 35.6 |
| 11 | CH$_2$ | 23.76 | 23.6 |
| 12 | CH(CH$_2$) | 121.93 (27.40) | 121.8 (27.50) |
| 13 | C(CH) | 145.42 (38.78) | 145.10 (39.0) |
| 14 | C | 41.95 | 41.80 |
| 15 | CH$_2$ | 26.21 | 26.2 |
| 16 | CH$_2$ | 27.16 | 27.0 |
| 17 | C | 32.72 | 32.50 |
| 18 | CH | 47.45 | 47.40 |
| 19 | CH$_2$(CH) | 47.05 (48.29) | 46.90 (48.10) |
| 20 | C(C) | 31.31 (150.97) | 31.30 (151.1) |
| 21 | CH$_2$ | 34.96 | 34.8 |
| 22 | CH$_2$ | 37.18 | 37.20 |
| 23 | CH$_3$ | 28.32 (26.92) | 28.20 |
| 24 | CH$_3$ | 15.71 (18.36) | 15.5 |
| 25 | CH$_3$ | 15.81 | 15.60 |
| 26 | CH$_3$ | 17.03 | 16.9 |
| 27 | CH$_3$ | 26.22 | 26.0 |
| 28 | CH$_3$ | 28.64 | 28.40 |
| 29 | CH$_3$(CH$_2$) | 33.56 (109.31) | 33.30 (109.5) |
| 30 | CH$_3$ | 23.75 (19.28) | 23.70 (19.5) |

Lupeol and β-Amyrin

Lupeol and β-amyrin are both pentacyclic triterpenes (de las Heras et al., 2003) that have been reported as anti-inflammatory agents (Safayhi et al., 1997; Safayhi and Sailer, 1997; Holanda Pinto et al., 2008). The triterpenic family of compounds to which these two isolated compounds belong, have been reported to possess antifungal and antibacterial activity. For instance, ursolic acid was identified as one of the active components in rosemary, claimed to inhibit growth of some food-associated bacteria and yeasts (Collins and Charles, 1987). Ursolic acid and its derivates inhibited the growth of Staphylococcus aureaus and Microsporium lenosum (Zeletova, 1986).

The triterpene, α- and β-amyrin, was isolated as a mixture (1:2) from the crude resin of Protium heptaphyllum and evaluated for antifungal properties against Candida albicans (ATCC 18804); Candida Krusei, Candida tropicalis, Candida parapsilosis and Candida glabrata (Johann et al., 2007). Esterification of α- and β-amyrin with a variety of acyl chlorides provided a series of analogue derivatives. Among the 15 derivatives, β- and β-amyrin formiate and α- and β-amyrin acetate were the most active, inhibiting all the Candida species tested in concentrations that ranged from 30 μg/ml to 250 μg/ml.

Minimal inhibitory concentration against C. albicans was: 125 μg/ml (α- and β-amyrin); 60 μg/ml (α- and β-formiate) and 250 μg/ml (α- and β-acetate) (Johann et al., 2007). These results support those of the current study where β-amyrin showed appreciable activity against C. albicans standard strain (ATCC 10231) (0.004 mg/ml) and six clinical isolates tested (Table 14).

α- and β-amyrin isolated from Eugenia umbelliflora were tested in vitro against a panel of standard and clinical isolates of human fungal pathogens (dermatophytes and opportunistic saprobes) and were found to be inactive against dermatophytes (*Epidermophyton floccosum, Microsporum canis, Microsporum gypseum, Trichophyton rubrum* and *Trichophyton mentagrophytes*) up to the maximum concentrations tested: 1000 µg/ml (Machado et al., 2009).

Tested against *Mycobacterium tuberculosis*, lupeol did not show any antibacterial activity (Chaiyadej et al., 2004; Suksamrarn et al., 2006; Gallo and Sarachine, 2009). In another investigation, lupeol was inactive against three bacteria species but revealed MICs of 63 µg/ml against *Enterococcus feacalis* (Shai et al., 2008). Lupeol was also inactive against *S. aureus, Salmonella typhi, Vibrio cholera, Escherichia coli, Shigella* spp. batch 0.57 (*S. dysentery; S. flexneri, S. sonnei* and *S. boydii*) displaying MICs>200 µg/ml (Mathabe et al., 2008). However, lupeol showed significant zones of inhibition in the cultures of 18 hospital strains of the Gram-negative bacteria *Pseudomonas aeruginosa* and *Klebsiella pneumonia* at a concentration of 30 µg/ml (Ahamed et al., 2007). Zones of inhibition was also observed in *P. aeruginosa, S. typhi* and *E. coli* cultures using lupeol acid-impregnated disks at a concentration of 10 mg/ml (Lutta et al., 2008), while lupeol acetate did not display any activity against Gram-negative bacteria and fungi, but displayed a strong antimicrobial effect against Gram-positive bacteria (Freire et al., 2002).

As an antifungal agent lupeol showed effects similar to its antibacterial activities concerning the effectiveness. Lupeol displayed moderate zones of inhibition in *Aspergillus niger, Aspergillus flavus, Rhizoctonia phaseoli* and *Penicillium chrysogenum* cultures at 1 mg/disc (Singh and Singh, 2003) while *A. niger* was significantly inhibited by 20(29)-lupene-3β-isoferulate at 0.01 mg/ml (Lall et al., 2006), confirming that stronger inhibition can be reached when C-3 position is esterified. However, Nguyen et al. (2007) synthesized several ester derivates from lupeol in the C-3 position (COMe, COCHMe$_2$, COP$_h$, COCH:CHP$_h$), which only yielded weak antimicrobial compounds.

In the current study lupeol showed appreciable activity against *C. albicans* standard strain (ATCC 10231) (0.004 mg/ml) and six clinical isolates tested (Table 14), but low selective activity against the fungal test organisms (Table 15). These results may suggest a cytotoxic effect for lupeol (LC$_{50}$=0.001481 µg/ml) (FIG. 16) against Mouse fibroblast cells. The results of the current study differ from those of Shai at al. (2008) where lupeol failed to display appreciable activity against *C. albicans* (250 µg/ml), but demonstrated high and selective activity against *Sporothrix schenckii* and *Microsporum canis*, 12 µg/ml and 16 µg/ml respectively. The authors explained those activities based on lupeols' cytotoxic LC$_{50}$ value (89.5 µg/ml) against monkey kidney (Vero) cells, suggesting a cytostatic action for lupeol (Shai et al., 2008). Additionally, lupeol was inactive against *Cryptococcus neoformans, Cladosporium cladosporioides* and *Cladosporium sphaerospermum* (Marqui et al., 2008).

Compound 2

Figure 20:
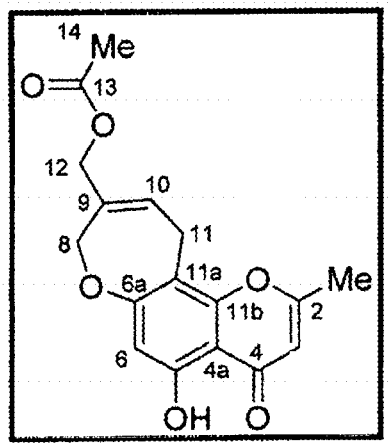
FIG. 20: Structure of Compound 2 isolated from *P. obliquum* leaves: 8,11-Dihydro-5-hydroxy-12-hydroxymethyl-2-methyl-4Hpyrano[2,3-g][1]benzoxepin-4-one 12-O-acetate
Figure 21:
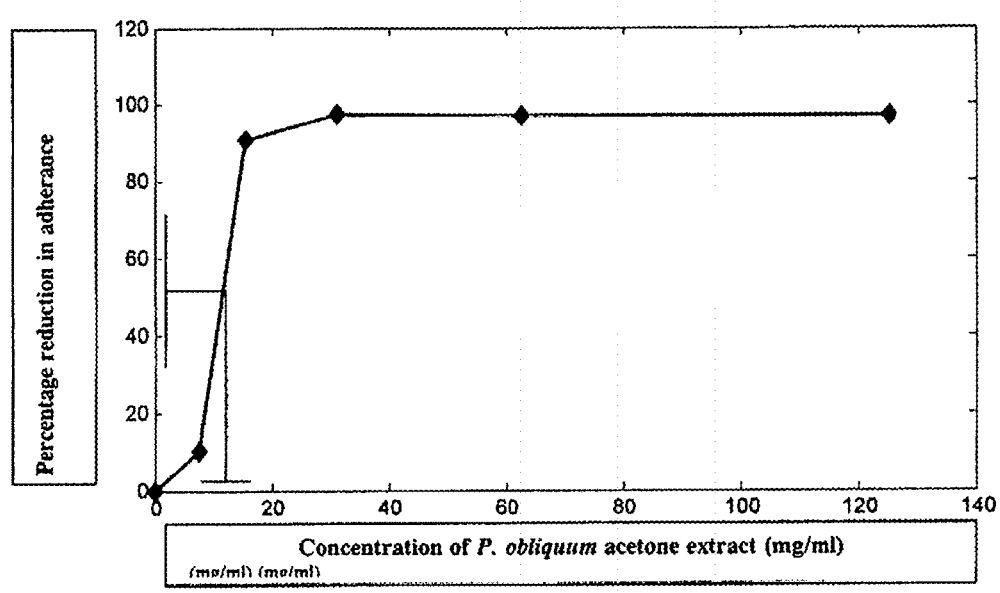
FIG. 21: Adhesion at $LC_{50}$ of *C. albicans* ATCC 10231 to human buccal epithelial cells following a 1-h exposure to various concentrations of *P. obliquum* acetone extract (mg/ml)

Compound 2 was obtained as a pure compound; the TLC fingerprint indicated unresolved single spot with three different mobile phases. 1D and 2D NMR spectra exhibited chemical shift characteristic of a novel compound. The compound was described as 8,11-Dihydro-5-hydroxy-12-hydroxymethyl-2-methyl-4H-pyrano[2,3-g][1]benzoxepin-4-one 12-O-acetate (FIG. 20). This compound has not yet been described in nature yet and we propose the trivial name obliquumol because it is an alcohol isolated from *P. obliquum*.

Figure 20: Structure of Compound 2 (novel compound) isolated from P. obliquum leaves: 8,11-Dihydro-5-hydroxy-12-hydroxymethyl-2-methyl-4-Hpyrano[2,3-g][1]benzoxepin-4-one 12-O-acetate

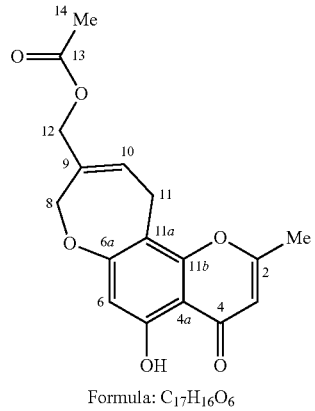

Formula: $C_{17}H_{16}O_6$
HR ESI: m/z 339.0840; calcd. for $C_{17}H_{16}O_6Na$; 339.0845.

TABLE 17

$^{13}$C NMR data of Compound 2 in CDCl$_3$ (for vleg1437 Candice 2) Bruker Avance III-400 spectrometer (Vleggar, 2011)

| Atom | Atom | $\delta_X$ | $\delta_H$ | HMBC (H→C) |
|---|---|---|---|---|
| 1 | 2 | 167.14 S | — | — |
| 2 | 3 | 108.66 D | 3 5.99 q (J 0.7) | C-2, C-4, C-4a, 2-CH$_3$ |
| 3 | 4 | 182.68 S | — | — |
| 4 | 4a | 106.72 S | — | — |
| 5 | 5 | 155.79 S | — | — |
| 6 | 6 | 99.29 D | 6.47 s | C-4, C-6a, C-5, C-11a, C-4a |
| 7 | 6a | 164.39 S | — | — |
| 8 | 8 | 71.04 T | 4 4.61 tt (J 1.6, 1.6) | C-6a, C-9, C-10, C-12, C-11 |
| 9 | 9 | 133.23 S | — | — |
| 10 | 10 | 128.30 D | 2 6.02 tt (J 5.5, 1.2) | C-11a, C-8, C-12, C-15 |
| 11 | 11 | 21.14 T | 6 3.52 d (J 5.6, 1.2, 1.6) | C-6a, C-11b, C-9, C-10, C-11a |
| 12 | 11a | 115.82 S | — | — |
| 13 | 11-b | 158.06 S | — | — |
| 14 | 12 | 66.45 T | 5 4.41 br s | C-9, C-10, C-8, C-13 |
| 15 | 2-Me | 20.78 Q | 7 2.30 d (J 0.7) | C-2, C-3 |
| 16 | 5-OH | — | 12.94 br s | — |
| 17 | 13 | 170.61 S | — | — |
| | 14 | 20.42 Q | 8 2.01 | C-13 |

In the current study the novel compound showed appreciable activity against *C. albicans* standard strain (ATCC 10231) (0.004 mg/ml) and six clinical isolates tested (Table 14), but low selective activity against the fungal test organisms (Table 15). These results may suggest a cytotoxic effect for 8,11-Dihydro-5-hydroxy-12-hydroxymethyl-2-methyl-4H-pyrano[2,3-g][1]benzoxepin-4-one 12-O-acetate (LC$_{50}$=7.232455 µg/ml) (FIG. 16) against Mouse fibroblast cells.

In this study the triterpenic compounds and novel compound tested, inhibited the growth of *C. albicans* standard strain (ATCC 10231) and clinical isolates with low MIC values (Table 14). Using bioautography the inhibition of growth of the fungal test species was clearly demonstrated, as indicated by clear zones on TLC chromatograms (FIG. 14). The activity observed with the isolated compounds further validates the traditional use of *P. obliquum* for treating fungal infections. The antifungal activity of lupeol; β-amyrin and 8,11-Dihydro-5-hydroxy-12-hydroxymethyl-2-methyl-4H-pyrano[2,3-g][1]benzoxepin-4-one 12-O-acetate are comparable with amphotericin B (Table 14). This is the first report of isolation and identification of compounds with antifungal activity from *P. obliquum* leaves.

Only obliquum (8,11-Dihydro-5-hydroxy-12-hydroxymethyl-2-methyl-4Hpyrano[2,3-g][1]benz oxepin-4-one 12-O-acetate) appeared safe enough to use as an anticandidal agent. This compound was much more active against the ATCC *C. albicans* strain than amphotericin B. This is a novel structure for an antifungal compound and changes to the chemical structure may increase the activity and reduce the toxicity of the compound.

Example 8

Adhesion of *Candida albicans* to Human Buccal Epithelial Cells (HBEC) in the Presence of *Ptaeroxylon obliquum* Acetone Leaf Extract Candidal adherence to human buccal epithelial cells (HBEC) is considered the critical initial step in the pathogenesis of oral candidiasis, which may eventually lead to a systemic infection, especially in immuno-compromised individuals (Schafer-Korting et al., 1996). The adherence of *Candida* to HBEC is a factor which influences the balance of oral clearance mechanisms, mucosal colonization and development of clinical signs of candidiasis.

Furthermore candidal adherence to the oral mucosa is intimately associated with all common forms of oral candidosis (Taweechaisupapong et al., 2005).

*Ptaeroxylon obliquum* (Thunb.) Radlk. is a medicinal plant used for several therapeutic purposes. For example, the powdered wood is used as a snuff to relieve headache and infusions of the powdered wood are taken for the treatment of rheumatism and heart disease (Watt and Breyer-Brandwijk, 1962). The bark is used for the treatment of rheumatism and arthritis (Pujol, 1990).

In the current study it was demonstrated that *P. obliquum* acetone leaf extract had antifungal activity towards *C. albicans* standard strain (ATCC 10231) and clinical isolates. In order to provide more information about the potential of *P. obliquum* acetone leaf extract for its development as a natural oral hygiene product, the inhibitory effects of *P. obliquum* acetone leaf extract on the in vitro adhesion of *C. albicans* standard strain (ATCC 10231) and two clinical isolates to human buccal epithelial cells (HBEC) was investigated.

In this example the inventors determined the ability of *C. albicans* standard strain (ATCC 10231) and two clinical isolates to adhere to healthy buccal epithelial cells (control); and to determine the ability of *C. albicans* standard strain (ATCC 10231) and two clinical isolates to adhere to HBEC in the presence of *Ptaeroxylon obliquum* acetone leaf extract.

Subjects

Buccal epithelial cells were taken from 20 healthy subjects (student volunteers) between 20 to 40 years old with no known co-existing disease or not taking any medication.

Ethical approval was obtained from the Ethics Committee of the Faculty of Health Sciences of the University of Pretoria, South Africa, and all individuals gave informed consent prior to their participation in this study.

Preparation of Yeast and Buccal Epithelial Cells

For preparation of yeast and buccal epithelial cells the methods of Taweechaisupapong et al., 2005 were used with some modification.

Yeast Cells

*C. albicans* standard strain (ATCC 10231) and clinical isolates were maintained on Sabouraud-dextrose agar and grown in the yeast phase in Sabouraud-dextrose broth for this study. The organisms were washed three times in normal saline (NSS) by centrifugation at 5000 rpm for 10 minutes and finally suspended in NSS to $4 \times 10^7$ cells/ml (MacFarlane standard 1).

Epithelial Cells

Human buccal epithelial cells (HBEC) were collected from healthy individual subjects by gently scraping the cheek mucosa with a sterile wooden spatula. To minimize individual variations, HBEC from the twenty healthy individuals were pooled in 10 ml of sterile NSS (Sandin et al., 1987). The pooled HBEC suspension was washed three times in NSS by centrifugation at 5000 rpm for 10 minutes to eliminate debris and loosely attached micro-organisms. Washed epithelial cells were confirmed to have no attached yeast before the adherence test. The HBEC was then re-suspended in NSS to a concentration of $9 \times 10^8$ cells/ml (by haemocytometer) and used immediately for the adhesion assay. The cells were collected at the same time of day on each occasion to minimize any possible effect of diurnal variations of HBEC on yeast adherence.

Preparation of the Antifungal Agent

Amphotericin B (Mast diagnostics) was used as the positive control antifungal agent. Minimal inhibitory concentration (MIC) values of *C. albicans* standard strain (ATCC 10231) and clinical isolates were determined by using the microplate dilution method developed by Eloff (1998b), with modifications for antifungal activity assay by Masoko et al. (2005). MIC values were regarded as the lowest concentration of amphotericin B that inhibited the growth of *C. albicans* standard strain (ATCC 10231) and clinical isolates. The minimal fungicidal concentration (MFC) values were determined as the lowest concentration of amphotericin B that inhibited 100 percent growth of *C. albicans* standard strain (ATCC 10231) and clinical isolates. The subcidal concentration values for amphotericin B towards *C. albicans* standard strain (ATCC 10231) and clinical isolates, used as positive control, in this study was the concentration slightly below the MFC of the drug. The MIC, MFC and subcidal concentration values for amphotericin B obtained in the present study are presented in Table 18.

TABLE 18

MIC, MFC and subcidal concentrations for amphotericin B

| | Candida albicans | | |
|---|---|---|---|
| | ATCC | Clinical isolates | |
| | 10231* | M0824 | 1051604 |
| *MIC (mg/ml) | 0.11 | 0.03 | 0.06 |
| *MFC (mg/ml) | 0.11 | 0.11 | 0.06 |
| Subcidal concentration | 0.11 | 0.06 | 0.06 |

*MIC: Minimal inhibitory concentration representing the mean value
*MFC: Minimal fungicidal concentration representing the mean value Preparation of *P. obliquum* Acetone Leaf Extract Leaves of *P. obliquum* were harvested from a tree on the Onderstepoort Campus of the University of Pretoria. The leaves were collected in loosely woven orange bags and dried in the dark at room temperature. The dried leaves were ground to powder using a Macsalab mill (Model 200 Lab). In a bulk extraction, powdered leaves (1000 g) of *P. obliquum* were extracted with acetone at room temperature. Approximately 79.52 g of extract was obtained from 1000 g of dried pulverized leaves. A *P. obliquum* acetone leaf extract (250 mg/ml) was used as the starting material for the subsequent study.

Adhesion Assay of *C. albicans* to HBEC after Exposure to *P. obliquum* Acetone Leaf Extract for One Hour Adhesion of *C. albicans* standard strain (ATCC 10231) and clinical isolates to HBEC was determined as follows: 0.2 ml of *P. obliquum* acetone leaf extract was serially two-fold diluted with normal saline (NSS) in tubes. Tubes containing 0.2 ml of amphotericin B and NSS served as positive and negative controls, respectively. 0.1 ml of HBEC and 0.1 ml of the yeast suspension prepared as described previously were added to each tube, mixed gently and incubated at 37° C. for 1 hour with gentle agitation. The suspension was then diluted in 1 ml of sterile NSS.

The cells were filtered through a 12 μm pore size polycarbonate filter (Millipore), and washed twice with 15 ml of sterile NSS to remove unattached fungi. Each filter was carefully removed with forceps and placed on a glass slide with the HBEC against the glass surface. After 30 s, the filter was gently removed; leaving the HBEC adhered to the glass slide. The slides were air-dried, fixed with methanol and stained with Gram's dye. The number of yeast cells adhering to 100 HBEC was determined by counting in a light microscopy (Nikon Trans microscope) at ×400 magnification and photographed with a Nixon digital camera DXM 1200 F.

The adhesion assay is a modification of a method previously described by Kimura and Pearsall (1978) and by Taweechaisupapong et al. (2005).

The numbers of fungi adhering per 100 human buccal epithelial cells were counted and the percentage reduction was determined as follows: crude plant extract concentration divided by the control (yeast+HBEC)×100 minus 100=% reduction.

The effect that *C. albicans* had on the structure of cells HBEC was also observed.

Each assay was performed with duplicate determinations. All slides were coded, images stored on CD, computer analysed and read without prior knowledge of treatments (blinded).

Figure 22:
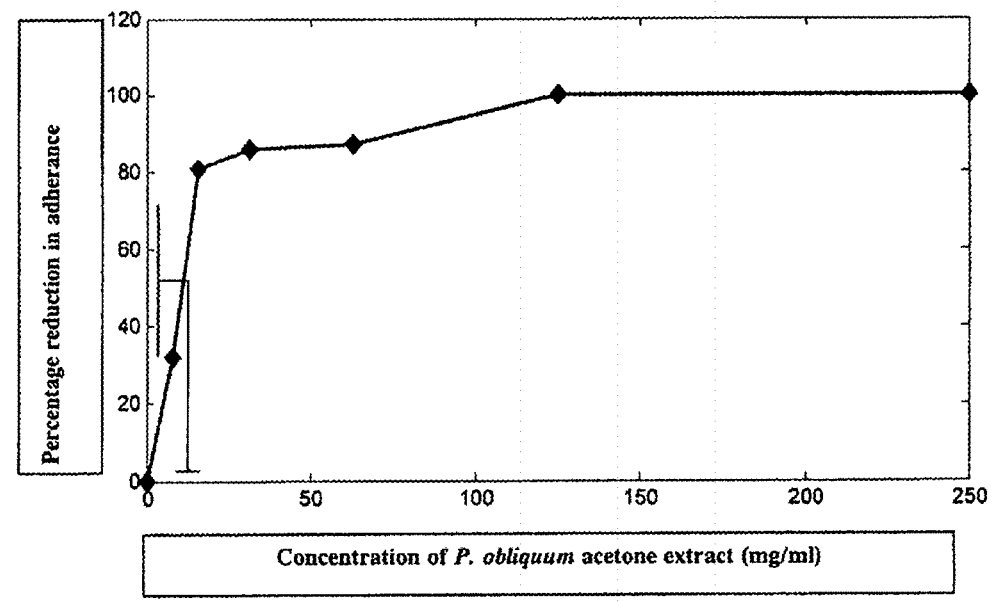
FIG. 22: Adhesion at $LC_{50}$ of *C. albicans* M0824 to human buccal epithelial cells following a 1-h exposure to various concentrations of *P. obliquum* acetone extract (mg/ml)
Figure 23:
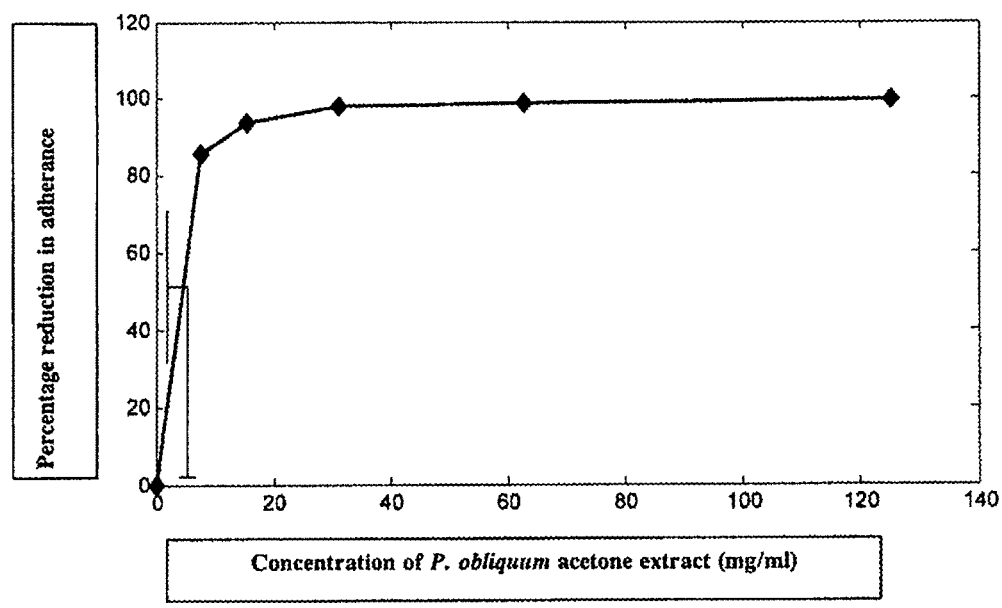
FIG. 23: Adhesion at $LC_{50}$ of *C. albicans* 1051604 to human buccal epithelial cells following a 1-h exposure to various concentrations of *P. obliquum* acetone extract (mg/ml).
Figure 24:
FIG. 24: *P. obliquum* acetone extract suppressing candidal adhesion to human buccal epithelial cells (HBEC)

Calculations according to the modified method of Taweechaisupapong et al., (2005) indicate that *P. obliquum* acetone extract at a concentration ≤250 mg/ml is capable of suppressing candidal adhesion to human buccal epithelial cells (HBEC) (FIG. 24) as effectively as subcidal concentrations of amphotericin B (Tables 19, 20 and 21). The adhesion values and the percentage reduction in the adhesion of *C. albicans* and two clinical isolates to HBEC, following a 1 hr exposure to various concentrations of *P. obliquum* acetone extract are presented in Tables 19, 20 and 21. If the $LC_{50}$ values are determined using graphs, (FIGS. 22, 22 and 23) it is evident that 50% adhesion of *C. albicans* cells are inhibited by concentration between 5 to 20 mg/ml, with a flattening off at concentrations above 20 mg/ml. Therefore it can be assumed that a much lower concentration of the extract can be used in a product to prevent candidal adhesion.

TABLE 19

Adhesion of *C. albicans* ATCC 10231 to human buccal epithelial cells following a 1-h exposure to various concentrations of *P. obliquum* acetone extract (mg/ml)

|  | Control | Amphotericin B | Concentration of *P. obliquum* acetone extract (mg/ml) | | | | | |
| --- | --- | --- | --- | --- | --- | --- | --- | --- |
|  | (Y + HBEC) | (0.11 mg/ml) | 7.8 | 15.6 | 31.2 | 62.5 | 125 | 250 |
| Number of yeast cells per 100 HBEC | 177 | 109 | 18 | 16 | 4 | 5 | 5 | 0 |
| Reduction in adherence % | 0 | 38.42 | 9.83 | 90.96 | 97.74 | 97.18 | 97.18 | 100 |

Y: yeast
HBEC: human buccal epithelial cells

TABLE 20

Adhesion of *C. albicans* M0824 to human buccal epithelial cells following a 1-h exposure to various concentrations of *P. obliquum* acetone extract (mg/ml)

|  | Control | Amphotericin B | Concentration of *P. obliquum* acetone extract (mg/ml) | | | | | |
| --- | --- | --- | --- | --- | --- | --- | --- | --- |
|  | (Y + HBEC) | (0.6 mg/ml) | 7.8 | 15.6 | 31.2 | 62.5 | 125 | 250 |
| Number of yeast per 100 HBEC | 182 | 12 | 124 | 35 | 25 | 23 | 0 | 0 |
| Reduction in adherence % | 0 | 93.41 | 31.86 | 80.76 | 86.26 | 87.36 | 100 | 100 |

Y: yeast
HBEC: human buccal epithelial cells

TABLE 21

Adhesion of *C. albicans* 1051604 to human buccal epithelial cells following a 1-h exposure to various concentrations of *P. obliquum* acetone extract(mg/ml)

|  | Control (Y + HBEC) | Amphotericin B (0.6 mg/ml) | Concentration of *P. obliquum* acetone extract (mg/ml) | | | | | |
|---|---|---|---|---|---|---|---|---|
|  |  |  | 7.8 | 15.6 | 31.2 | 62.5 | 125 | 250 |
| Number of yeast per 100 HBEC | 202 | 10 | 29 | 13 | 4 | 2 | 1 | 0 |
| Reduction in adherence % | 0 | 95.05 | 85.64 | 93.56 | 98.02 | 99.00 | 99.58 | 100 |

Y: yeast
HBEC: human buccal epithelial cells

Figure 25:
FIG. 25: Normal human buccal epithelial cells (HBEC)

The development of the microscopy techniques and computer programmes, used in this study, with which the images can be studied made it possible to observe the effects the yeast cells have on human buccal epithelial cells (HBEC) (FIG. 25). The percentage reduction in adherence can be correlated to the destruction of the epithelial cells where the growth of the *C. albicans* cells was not inhibited by *P. obliquum* acetone extract.

Figure 26:
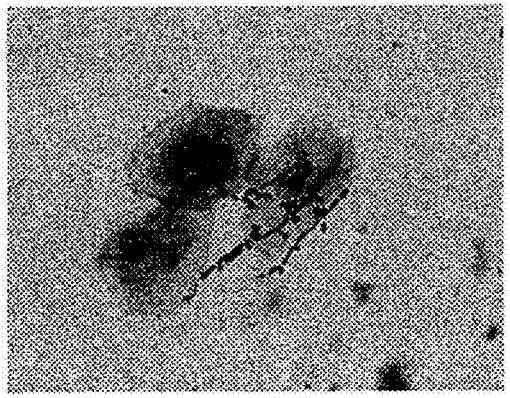
FIG. 26: In the presence of amphotericin B (control) the *C. albicans* cells were attaching, budding and forming hyphae
Figure 27:
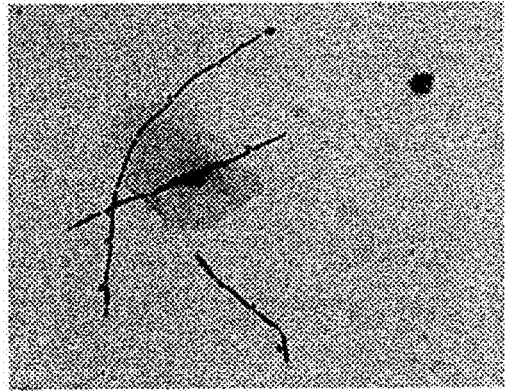
FIG. 27: In the presence of amphotericin B (control) the *C. albicans* cells were attaching, budding and forming hyphae
Figure 28:
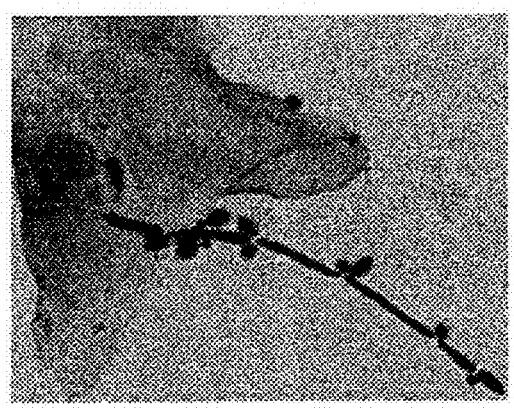
FIG. 28: In the presence of lower concentrations of *P. obliquum* acetone extract the *C. albicans* cells were attaching, budding and forming hyphae
Figure 29:
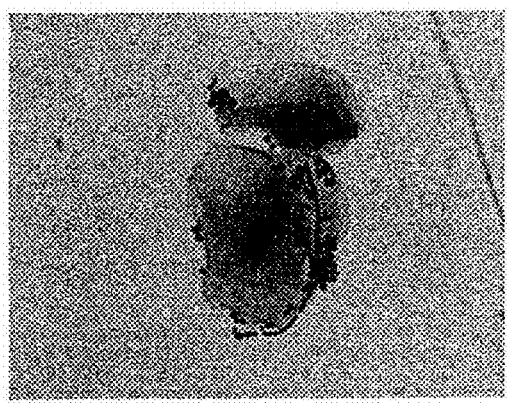
FIG. 29: In the presence of lower concentrations of *P. obliquum* acetone extract the *C. albicans* cells were attaching, budding and forming hyphae
Figure 30:
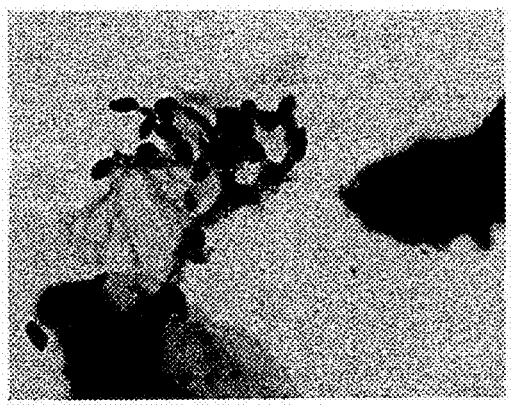
FIG. 30: At lower concentrations of *P. obliquum* acetone extract, and in the presence of amphotericin B, the *C. albicans* cells attack the HBEC and completely destroyed the epithelial cells
Figure 31:
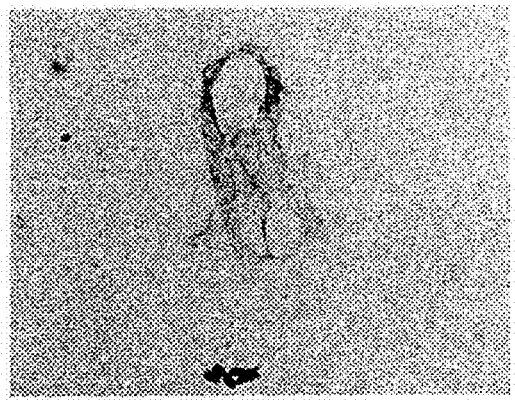
FIG. 31: At lower concentrations of *P. obliquum* acetone extract, and in the presence of amphotericin B, the *C. albicans* cells attack the HBEC and completely destroyed the epithelial cells
Figure 32:
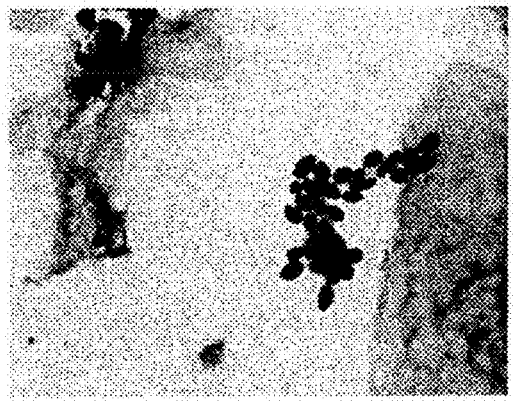
FIG. 32: At lower concentrations of *P. obliquum* acetone extract high numbers of *C. albicans* cells attached to an epithelial cell and were able to destroy the nucleus and structure of the epithelial cell
Figure 33:
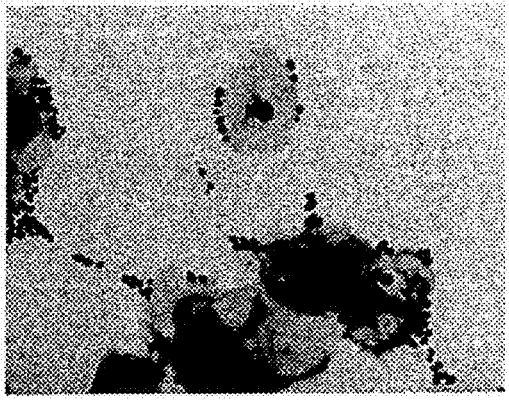
FIG. 33: At lower concentrations of *P. obliquum* acetone extract high numbers of *C. albicans* cells attached to an epithelial cell and were able to destroy the nucleus and structure of the epithelial cell

Visual evaluation of HBEC strain revealed that in the presence of amphotericin B (control) at xxmg/ml the *C. albicans* cells were budding and forming hyphae (FIGS. 26 and 27). This was observed in both the attached and un-attached *C. albicans* cells. The same was observed at lower concentrations of *P. obliquum* acetone extract (FIGS. 28 and 29). At these lower concentrations, and in the presence of amphotericin B, the *C. albicans* cells attack the HBEC and completely destroyed the epithelial cells (FIGS. 30 and 31). It is well known that mycelial forms of *C. albicans* adhere more efficiently to host cells than do yeast form cells (Kimura and Pearsall, 1980; Pendrak and Klotz, 1995). It was also observed in the current study, that where high numbers of *C. albicans* cells attached to an epithelial cell, the yeast cells started to destroy the nucleus and structure of the epithelial cell (FIGS. 32 and 33). This correlates with a high incidence of candidiasis in the oral cavity where the epithelial cells are destroyed by the attachment of the yeast cells (Samaranayake, 1990; Samaranayake et al., 1994; Taweechaisupapong et al., 2005).

The observed suppression of *Candida* adherence to HBEC in the presence of *P. obliquum* acetone extract suggests the potential development of a natural oral hygiene product. The concentration at which 100% suppression occurred was probably too high to be of practical use, but a concentration of c. 20 mg/ml lead to a 90% reduction of adhesion. Based on the toxicity of the acetone extracts this may not be a feasible practical application.

Example 9

In Vitro Biological Activity of the *Ptaeroxylon obliquum* Leaf Extracts Collected from Different Localities Plant leaf materials of *Ptaeroxylon obliquum* were collected from the Pretoria National Botanical Gardens, Kwazulu Natal Botanical Gardens and University of Pretoria, Onderstepoort campus in the same season. All the leaf extracts were extracted in acetone. The bulk powdered leaves of *P. obliquum* were extracted with acetone and fractionated into five fractions (Hexane, chloroform, 30% $H_2O$ in methanol, butanol, and $H_2O$) using solvent-solvent fractionation as described by Suffness and Douros (1979), to group the phytochemicals based on polarity.

The isolation of the bioactive compounds from the crude extracts of *P. obliquum* was undertaken at the Phytomedicine Programme labs. To date, four compounds have been isolated from the non-polar fractions using column chromatography and silica gel as the stationary phase. The structures of the compounds were characterized and elucidated using Nuclear Magnetic Resonance (NMR) and Mass spectrometry. One of the compounds isolated was isolated for the first time in plants by the inventors. Two of the compounds were tested for antibacterial, antifungal, anti-mycobacterial and anthelminthic activity. The same methods as previously described were used for the crude and purified fractions.

Antifungal Activity of the Crude Extracts, Fractions and Isolated Compounds from *P. obliquum* Against Clinical Isolates of Opportunistic Fungal Strains The microplate dilution method (Eloff, 1998), with slight modification (Masoko et al., 2005) was used to test the antifungal activity of the crude extracts, fractions and isolated compounds from *P. obliquum*. Clinical isolates of the four opportunistic fungal strains *Aspergillus fumigatus, Candida albicans, Crytococcus neoformans* and *Candida albicans* ATCC 10231 were used to test for antifungal activity.

The results obtained from crude extracts of the *P. obliquum* indicated that, at least in this case, environmental factors do not play a major role in antifungal activity (Table 22). The hexane fraction was more active than all of the other fractions when tested on the fungi. An MIC value of 40 µg/ml was obtained against *A. fumigatus* (Table 23).

TABLE 22

Minimal inhibitory concentration (MIC) values of the acetone crude extracts of *Ptaeroxylon obliquum* collected from different localities tested against the four animal fungi

| Fungal strain | MIC in mg/ml | | |
|---|---|---|---|
|  | $PO_{Sanbi}$ | $PO_{Kzn}$ | $PO_{Onder}$ |
| *Aspergillus fumigatus* | 0.16 | 0.32 | 0.16 |
| *Candida albicans* ATCC | 0.32 | 0.16 | 0.32 |
| *Candida albicans* | 0.32 | 0.16 | 0.63 |
| *Cryptococcus neoformans* | 0.32 | 0.32 | 0.63 |

TABLE 23

Minimal inhibitory concentration (MIC) values in mg/ml of the five fractions of *P. obliquum* collected from Sanbi tested against the four fungi

| Fungal strain | MIC in mg/ml | | | | |
|---|---|---|---|---|---|
|  | Hexane | $CHCL_3$ | 30% $H_2O$ | $H_2O$ | Butanol |
| *Aspergillus fumigatus* | 0.04 | 0.16 | 0.16 | 2.5 | 1.25 |
| *Candida albicans* ATCC | 0.08 | 0.63 | 1.25 | 2.5 | 1.25 |
| *Candida albicans* | 0.16 | 0.32 | 0.32 | 2.5 | 2.5 |
| *Cryptococcus neoformans* | 0.08 | 0.16 | 0.32 | 2.5 | 1.25 |

TABLE 24

Minimal inhibitory concentration (MIC) values in µg/ml of the compounds isolated from the chloroform fraction tested against four fungi

| | MIC in µg/ml | | |
|---|---|---|---|
| Fungal strain | Obliquumol | Obliquumol derivative | Lupeol and β amyrin |
| *Aspergillus fumigatus* | 16 | 62.5 | 32 |
| *Candida albicans* ATCC | 2 | 8 | 16 |
| *Candida albicans* | 62.5 | 31.5 | 125 |
| *Cryptococcus neoformans* | 8 | 16 | 16 |

Both the obliquumol and the mixture had good antifungal activity. Obliquumol was more active than the antifungal drug Amphotericin B against *C. neoformans* and *C. albicans* (ATCC), both of these fungi are problematic in immuno-compromised patients.

Antifungal Activity of the Crude Extracts, Fractions and Isolated Compounds from *P. obliquum* Against Plant Pathogenic Fungal Strains The antifungal activity of the crude extracts and the five fractions were also tested against 10 plant pathogenic fungi (*Aspergillus niger, Aspergillus parasiticus, Colletotrichum gloeosporioides, Fusarium oxysporum, Penicillium digitum, Penicillium expansum, Penicillium italicum, Penicillium janthinellum, Trichoderma harzianum* and *Rhizoctonia solani*).

The crude extracts and the fractions had antifungal activity against all the 10 tested plant pathogenic fungi. The crude extracts and hexane fraction had the most promising activity against *A. niger* and *P. digitum* with an MIC of 80 µg/ml for both.

The obliquumol was more active against *R. solani* and *T. harzianum* with MICs of 8 µg/ml and 16 µg/ml respectively. The mixture also had some good active against *R. solani* with an MIC of 16 µg/ml.

TABLE 24

Minimal inhibitory concentration (MIC) values of the acetone crude extracts of *Ptaeroxylon obliquum* collected from different localities tested against ten plant pathogenic fungi

| | MIC in mg/ml | | |
|---|---|---|---|
| Plant pathogen | Crude (KZN) | Crude (OP) | Crude (Sanbi) |
| *Aspergillus niger* | 0.08 | 0.08 | 0.08 |
| *Aspergillus parasiticus* | 0.32 | 0.32 | 0.32 |
| *Colletotrichum gloeosporioides* | 0.16 | 0.32 | 0.08 |
| *Fusarium oxysporum* | 0.32 | 0.63 | 0.63 |
| *Penicillium digitum* | 0.16 | 0.08 | 0.08 |
| *Penicillium expansum* | 0.32 | 0.32 | 0.32 |
| *Penicillium italicum* | 0.16 | 0.63 | 0.16 |
| *Penicillium janthinellum* | 0.32 | 0.32 | 0.32 |
| *Trichoderma harzianum* | 0.32 | 0.32 | 0.63 |
| *Rhizoctonia solani* | 0.63 | 1.25 | 1.25 |

TABLE 25

Minimal inhibitory concentration (MIC) values of the five fractions of *P. obliquum* collected from Sanbi tested against ten plant fungi

| | MIC in mg/ml | | | | |
|---|---|---|---|---|---|
| Plant pathogen | Hexane | CHCL₃ | 30% H₂O | Butanol | H₂O |
| *Aspergillus niger* | 0.08 | 0.16 | 0.32 | 0.63 | 2.50 |
| *Aspergillus parasiticus* | 0.32 | 0.63 | 0.63 | 1.25 | >2.50 |
| *Colletotrichum gloeosporioides* | 0.16 | 0.16 | 0.32 | 0.32 | 2.50 |
| *Fusarium oxysporum* | 0.63 | 0.32 | 0.32 | 1.25 | 2.50 |
| *Penicillium digitum* | 0.08 | 0.32 | 0.32 | 1.25 | >2.50 |
| *Penicillium expansum* | 0.32 | 0.32 | 0.63 | 1.25 | >2.50 |
| *Penicillium italicum* | 0.16 | 0.63 | 0.63 | 1.25 | >2.50 |
| *Penicillium janthinellum* | 0.32 | 0.32 | 0.63 | 1.25 | >2.50 |
| *Trichoderma harzianum* | 0.32 | 0.63 | 0.63 | 1.25 | 2.50 |
| *Rhizoctonia solani* | 1.25 | 0.63 | 1.25 | 1.25 | >250 |

TABLE 26

Minimal inhibitory concentration (MIC) values of the compounds isolated from the chloroform fraction tested pathogenic fungi

| | MIC in µg/ml | |
|---|---|---|
| Plant pathogen | Obliquumol | Lupeol and β-amyrin mixture |
| *Aspergillus niger* | 32 | 125 |
| *Aspergillus parasiticus* | 250 | >250 |
| *Colletotrichum gloeosporioides* | 32 | 63 |
| *Fusarium oxysporum* | 63 | 63 |
| *Penicillium digitum* | 32 | 32 |
| *Penicillium expansum* | 32 | 125 |
| *Penicillium italicum* | 125 | >250 |
| *Penicillium janthinellum* | 63 | 63 |
| *Trichoderma harzianum* | 16 | 32 |
| *Rhizoctonia solani* | 8 | 16 |

Anti-Mycobacterial Activity of the Crude Extracts, Fractions and Isolated Compounds from *P. obliquum*

The serial microplate dilution method developed by Eloff (1998) was used to determine the minimal inhibitory concentration (MIC) of the crude extracts, fractions and isolated compounds from *P. obliquum* against several mycobacterial strains. The anti-mycobacterial efficacy was tested against the fast growing and non-pathogenic *Mycobacterium* species *Mycobacterium aurum, Mycobacterium bovis, Mycobacterium fortuitum* and *Mycobacterium smegmatis*.

Acetone crude extracts of *P. obliquum* leaves collected from Kwazulu Natal were found to be more active than crude extracts from leaves obtained from the Pretoria National Botanical Gardens and the University of Pretoria, Onderstepoort campus, against all of the mycobacteria tested. MIC value as low as 20 µg/ml were obtained with the Kwazulu Natal crude extracts against *M. fortuitum*. The hexane fraction was the most active with MIC values ranging from 20-80 µg/ml. The obliquumol was more active against *M. fortuitum* and *M. smegmatis* with MIC values of 8 µg/ml and 16 µg/ml respectively. The activity of the obliquumol when tested against *M. bovis* provided a MIC value of 31.5 µg/ml.

TABLE 27

Minimal inhibitory concentration (MIC) values of the acetone crude extracts of *Ptaeroxylon obliquum* collected from different localities tested against the four mycobacteria

| | MIC in mg/ml | | |
|---|---|---|---|
| Mycobacterial species | $PO_{Sanbi}$ | $PO_{Kzn}$ | $PO_{Onder}$ |
| *Mycobacterium aurum* | 0.32 | 0.08 | 0.16 |
| *Mycobacterium bovis* | 0.16 | 0.08 | 0.16 |
| *Mycobacterium fortuitum* | 0.08 | 0.02 | 0.08 |
| *Mycobacterium smegmatis* | 0.32 | 0.16 | 0.32 |

TABLE 28

Minimal inhibitory concentration (MIC) values of the five fractions of *P. obliquum* collected from Sanbi tested against the four mycobacteria

| | MIC in mg/ml | | | | |
|---|---|---|---|---|---|
| Mycobacterial species | Hexane | $CHCL_3$ | 30% $H_2O$ | $H_2O$ | Butanol |
| *Mycobacterium aurum* | 0.08 | 1.25 | 0.63 | 2.5 | 1.25 |
| *Mycobacterium bovis* | 0.08 | 0.63 | 0.32 | 2.5 | 1.25 |
| *Mycobacterium fortuitum* | 0.02 | 0.08 | 0.04 | 0.63 | 0.32 |
| *Mycobacterium smegmatis* | 0.08 | 0.63 | 0.32 | 2.5 | 1.25 |

TABLE 29

Minimal inhibitory concentration (MIC) values of the compounds isolated from the chloroform fraction tested against four mycobacteria

| | MIC in µg/ml | | |
|---|---|---|---|
| Mycobacterial species | Obliquumol | Obliquumol derivative | Lupeol & β-amyrin mixture |
| *Mycobacterium aurum* | 125 | 250 | >250 |
| *Mycobacterium bovis* | 31.5 | 62.5 | 250 |
| *Mycobacterium fortuitum* | 8 | 250 | 62.5 |
| *Mycobacterium smegmatis* | 16 | 62.5 | 62.5 |

Antibacterial Activity of the Crude Extracts, Fractions and Isolated Compounds from *P. obliquum*

The serial microplate dilution method developed by Eloff (1998) was used to determine the minimal inhibitory concentration (MIC) of the crude extracts, fractions and isolated compounds from *P. obliquum* against several bacterial strains. The antimicrobial activity was determined against the bacterial strains *Escherichia coli* ATTC 27853, *Escherichia coli* ATTC 6739, *Enterococcus faecalis* ATCC 29212, *Pseudomonas aeruginosa* ATCC 25922, *Staphylococcus aureus* ATCC 6538, *Staphylococcus aureus* ATCC 29213, *Salmonella typhi* ATCC 14028.

All of the acetone extracts showed good antibacterial activity, inhibiting growth of the bacteria at concentrations ranging from 40-320 µg/ml. The variation in antibacterial activity based in geographical location was minimal. The crude extracts from different geographical locations showed good activity mainly against *S. aureus* ATCC 6538. The non-polar fractions (Hexane and chloroform) were the most active compared to the polar fractions.

The obliquumol showed more activity than lupeol and amyrin mixture against all of the bacteria tested, with an MIC value of 31.5 µg/ml for a number of the bacteria.

TABLE 30

Minimal inhibitory concentration (MIC) values of the acetone crude extracts of *Ptaeroxylon obliquum* collected from different localities tested against the different bacterial strains

| | MIC in mg/ml | | |
|---|---|---|---|
| Bacterial strain | $PO_{Sanbi}$ | $PO_{Kzn}$ | $PO_{Onder}$ |
| *Escherichia coli* ATTC 27853 | 0.24 | 0.16 | 0.24 |
| *Escherichia coli* ATTC 6739 | 0.32 | 0.16 | 0.16 |
| *Enterococcus faecalis* ATCC 29212 | 0.24 | 0.24 | 0.16 |
| *Pseudomonas aeruginosa* ATCC 25922 | 0.24 | 0.24 | 0.24 |
| *Staphylococcus aureus* ATCC 29213 | 0.12 | 0.12 | 0.1 |
| *Staphylococcus aureus* ATCC 6538 | 0.16 | 0.04 | 0.08 |
| *Salmonella typhi* ATCC 14028 | 0.16 | 0.16 | 0.16 |

TABLE 31

Minimal inhibitory concentration (MIC) values of the five fractions of *P. obliquum* collected from Sanbi tested against the different bacterial strains

| | MIC in mg/ml | | | | |
|---|---|---|---|---|---|
| Bacterial strain | Hexane | $CHCL_3$ | 30% $H_2O$ | $H_2O$ | Butanol |
| *Escherichia coli* ATTC 27853 | 0.08 | 0.24 | 0.63 | 2.5 | 1.25 |
| *Escherichia coli* ATTC 6739 | 0.32 | 0.32 | 0.32 | 0.63 | 0.63 |
| *Enterococcus faecalis* ATCC 29212 | 0.08 | 0.08 | 32 | 2.5 | 1.25 |
| *Pseudomonas aeruginosa* ATCC 25922 | 0.16 | 0.32 | 0.63 | 2.5 | 1.25 |
| *Staphylococcus aureus* ATCC 29213 | 0.04 | 0.24 | 0.32 | 0.63 | 0.63 |
| *Staphylococcus aureus* ATCC 6538 | 0.16 | 0.16 | 0.32 | 0.63 | 0.63 |
| *Salmonella typhi* ATCC 14028 | 0.32 | 0.32 | 0.63 | 0.63 | 0.63 |

TABLE 32

Minimal inhibitory concentration (MIC) values of the compounds isolated from the chloroform fraction tested against seven bacterial strains

| | MIC in µg/ml | |
|---|---|---|
| Bacterial species | Obliquumol | Lupeol and amyrin mixture |
| *Escherichia coli* ATTC 27853 | 80 | 80 |
| *Escherichia coli* ATTC 6739 | 80 | 160 |
| *Enterococcus faecalis* ATCC 29212 | >250 | >250 |
| *Pseudomonas aeruginosa* ATCC 25922 | 31.5 | 62.5 |
| *Staphylococcus aureus* ATCC 29213 | 31.5 | 62.5 |
| *Staphylococcus aureus* ATCC 6538 | 31.5 | 62.5 |
| *Salmonella typhi* ATCC 14028 | 31.5 | 31.5 |

Antihelminthic Activity of the Acetone Crude Extract and the Isolated Compound from *P. obliquum*

The results for the antihelminthic activity of the acetone crude extract and the obliquumol compound isolated from *P. obliquum* are presented in Table 33. The extract and isolated compound were tested for activity on *Haemonchus contortus*. The crude extract had promising activity in both egg hatch assay (EHA) and the larval development test (LDT)

with EC$_{50}$ of 3.0797 mg/ml and 2.2057 mg/ml respectively. Adamu et al (2013) suggested that extracts with EC$_{50}$ greater than 6 mg/ml should be considered to have weak antihelminthic activity because of the difficulties in achieving such high concentrations when administering compounds to animals.

The novel compound isolated from the leaves of *P. obliquum* was more efficacious than the crude extract in both EHA and LDT with EC$_{50}$ as low as 95.6 µg/ml when the compound was tested against larvae, the results which are also comparable with other active compounds against *H. contortus* (Lounasmaa et al., 1973: Bosman et al., 2004: Adamu et al., 2013). Although the selective index of the crude extract was low, the low toxicity of the compound against Vero cells shows that the novel compound is a good subject for further investigation.

TABLE 33

Antihelminthic activity of the acetone crude extract and obliquumol isolated from *P. obliquum* on the egg and larva of *Haemonchus contortus* together with cytotoxicity on Vero monkey kidney cells and the selective index

|  | Antihelminthic activity EC$_{50}$ (mg/ml) | | Cytotoxicity | Selective index | |
| --- | --- | --- | --- | --- | --- |
|  | EDA | LDT | LC$_{50}$ (mg/ml) | EDA | LDT |
| Crude extract | 3.0797 ± 0.0482 | 2.2057 ± 0.1779 | 0.0142 ± 0.006 | 0.0046 | 0.0064 |
| Obliquumol | 0.2235 ± 0.0286 | 0.0956 ± 0.0020 | >200 | ** | ** |

EHA: Egg hatch assay.
LDT: Larval development test,
**: not calculated

Example 10

Cytotoxicity of the Crude Extracts, Fractions and the Isolated Compounds

Results for the cytotoxicity of the crude, fractions and the isolated compounds are presented in Table 35. All of the tested samples had some level of toxicity against both Vero cells and human liver cells. The human liver (C3A) cells were more resistant to the toxicity of the samples but were more susceptible to the positive control, doxorubicin, which is a common phenomenon. The fractionation of the crude extract increased toxicity with all of the tested fractions on both Vero cells and human liver C3A cells. However, obliquumol was less toxic with an IC$_{50}$ of at least greater than 200 µg/ml. The semi-synthesized derivative of the obliquumol was relatively toxic against the Vero cells with an LC$_{50}$ of 85 µg/ml compared to the other tested samples.

TABLE 34

Cytotoxicity of the acetone crude extract, three fractions (hexane, chloroform and 30% H$_2$O in methanol) and the isolated compounds from *P. obliquum* tested on the Vero monkey kidney cells and human liver (C3A) cells

|  | Cytotoxicity LC$_{50}$ (mg/ml) | |
| --- | --- | --- |
|  | Vero cells | C3A cells |
| Crude extract | 0.0142 ± 0.0056 | 0.1065 ± 0.023 |
| Hexane fraction | 0.0287 ± 0.0287 | 0.0667 ± 0.024 |
| CHL$_3$ fraction | 0.0291 ± 0.0005 | 0.0943 ± 0.007 |
| 30% H$_2$0 in MeOH fraction | 0.0496 ± 0.0050 | 0.0737 ± 0.001 |
| Obliquumol | >200 | >200 |
| Obliquumol derivative | 85.6952 ± 3.4412 | 126.509 ± 25.750 |
| Lupeol & β-amyrin mixture | 130.6736 ± 7.317 | >200 |
| Doxorubicin (uM) | 2.5147 ± 0.2027 | 0.1163 ± 0.0174 |

Those skilled in the art will recognise and/or be able to ascertain using no more than routine experimentation, many equivalents to the specific embodiments of the disclosure described herein. Such equivalents are intended to be encompassed by the following claims.

The invention claimed is:

1. A method of treating a subject for an infection, the method comprising administering to the subject an effective amount of a compound having a formula (I):

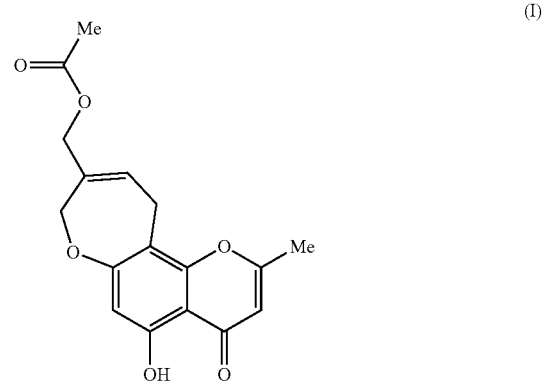 [SMILES: CC(=O)OCC1=CCc2c(cc(O)c3c(=O)cc(C)oc23)OC1]

or a pharmaceutically acceptable salt thereof; and wherein the infection is a fungal, bacterial or helminthic infection.

2. The method of claim 1, wherein the infection is a bacterial infection caused by a bacterium selected from the group consisting of *Acinetobacter* spp., *Actinobacillus* spp., *Actinomycetes* spp., *Aeromonas* spp., *Bacillus* spp., *Bordetella* spp., *Borrelia* spp., *Brucella* spp., *Campylobacter* spp., *Chlamydia* spp., *Clostridium* spp., *Corynebacterium* spp., *Enterobacter* spp., *Enterococcus* spp., *Envinia* spp., *Erysipelothrix* spp., *Escherichia* spp., *Francisella* spp., *Klebsiella* spp., *Haemophilus* spp., *Legionella* spp., *Leptospira* spp.,

*Listeria* spp., *Moraxella* spp., *Mycobacterium* spp., *Mycoplasma* spp., *Neisseria* spp., *Nocardia* spp., *Pasteurella* spp., *Pseudomonas* spp., *Rickettsia* spp., *Salmonella* spp., *Shigella* spp., *Spirillum* spp., *Staphylococcus* spp., *Streptobacillus* spp., *Streptococcus* spp., *Streptomyces* spp., *Treponema* spp., *Vibrio* spp., *Yersinia* spp. and *Xanthomonas* spp.

3. The method of claim 1, wherein the bacterial infection is caused by a bacterium selected from the group consisting of *Escherichia coli, Enterococcus faecalis, Mycobacterium aurum, Mycobacterium bovis, Mycobacterium fortuitum, Mycobacterium smegmatis, Pseudomonas aeruginosa, Staphylococcus aureus* and *Salmonella typhi*.

4. The method of claim 1, wherein the infection is a fungal infection caused by a fungus selected from the group consisting of *Alternaria* spp., *Aspergillus* spp., *Candida* spp., *Cercospora* spp., *Cladosporium* spp., *Colletotrichum* spp., *Cryptococcus* spp., *Diplodia* spp., *Fusarium* spp., *Guignardia* spp., *Monilinia* spp., *Penicillium* spp., *Phytophthora* spp., *Plasmopara* spp., *Podosphaera* spp., *Puccinia* spp., *Pythium* spp., *Rhizoctonia* spp., *Rhizopus* spp., *Sclerotinia* spp., *Sphaerotheca* spp., *Trichoderma* spp., *Venturia* spp. and *Verticillium* spp.

5. The method of claim 1, wherein the fungal infection is caused by a fungus selected from the group consisting of *Aspergillus fumigatus, Aspergillus niger, Aspergillus parasiticus, Candida albicans, Colletotrichum gloeosporioides, Cryptococcus neoformans, Fusarium oxysporum, Penicillium digitum, Penicillium expansum, Penicillium italicum, Penicillium janthinellum, Trichoderma harzianum* and *Rhizoctonia solani*.

6. The method of claim 1, wherein the helminthic infection is caused by a helminth selected from the consisting of *Ascaris* spp., *Ancylostoma* spp., *Haemonchus* spp., *Strongoloides* spp., *Necator* spp., *Trichuris* spp. and *Uncinaria* spp.

7. The method of claim 1, wherein the helminthic infection is caused by *Haemonchus contortus*.

8. The method of claim 1, wherein the subject is a mammal.

9. The method of claim 1, wherein the subject is a plant.

\* \* \* \* \*